(12) United States Patent
Gilbertson et al.

(10) Patent No.: US 7,192,592 B2
(45) Date of Patent: *Mar. 20, 2007

(54) METHODS FOR PROMOTING GROWTH OF BONE, LIGAMENT, AND CARTILAGE USING ZVEGF4

(75) Inventors: Debra G. Gilbertson, Seattle, WA (US); Charles E. Hart, Woodinville, WA (US)

(73) Assignee: ZymoGenetics, Inc., Seattle, WA (US)

( * ) Notice: Subject to any disclaimer, the term of this patent is extended or adjusted under 35 U.S.C. 154(b) by 89 days.

This patent is subject to a terminal disclaimer.

(21) Appl. No.: 10/910,938

(22) Filed: Aug. 3, 2004

(65) Prior Publication Data

US 2005/0031694 A1    Feb. 10, 2005

Related U.S. Application Data

(60) Continuation of application No. 10/226,559, filed on Aug. 23, 2002, now Pat. No. 6,866,991, which is a division of application No. 09/540,224, filed on Mar. 31, 2000, now Pat. No. 6,468,543.

(60) Provisional application No. 60/180,169, filed on Feb. 4, 2000, provisional application No. 60/164,463, filed on Nov. 10, 1999, provisional application No. 60/132,250, filed on May 3, 1999.

(51) Int. Cl.
| | |
|---|---|
| A61K 39/00 | (2006.01) |
| A61K 9/14 | (2006.01) |
| A01N 38/00 | (2006.01) |
| C07K 14/00 | (2006.01) |
| C07K 17/00 | (2006.01) |

(52) U.S. Cl. .................. 424/198.1; 514/2; 530/350; 530/399; 424/484

(58) Field of Classification Search ............ None
See application file for complete search history.

(56) References Cited

U.S. PATENT DOCUMENTS

| | | | |
|---|---|---|---|
| 4,874,746 A | 10/1989 | Antoniades et al. | 514/21 |
| 5,124,316 A | 6/1992 | Antoniades et al. | 514/12 |
| 5,533,836 A | 7/1996 | Moore | 435/240.31 |
| 5,770,228 A | 6/1998 | Edwards et al. | 424/488 |

(Continued)

FOREIGN PATENT DOCUMENTS

EP    0 289 584    5/1993

(Continued)

OTHER PUBLICATIONS

Midy et al., *Biochem. Biophys. Res. Comm.* 199(1): 380-386, 1994.

(Continued)

*Primary Examiner*—Brenda Brumback
*Assistant Examiner*—Shulamith H Shafer
(74) *Attorney, Agent, or Firm*—Gary Parker

(57) ABSTRACT

Methods for promoting growth of bone, ligament, or cartilage in a mammal are disclosed. The methods comprise administering to said mammal a composition comprising a pharmacologically effective amount of zvegf4 in combination with a pharmaceutically acceptable delivery vehicle. Also disclosed are methods for promoting proliferation or differentiation of osteoblasts, osteoclasts, chondrocytes, or bone marrow stem cells comprising culturing the cells in an effective amount of zvegf4.

10 Claims, 8 Drawing Sheets

U.S. PATENT DOCUMENTS

| | | | |
|---|---|---|---|
| 5,863,297 A | 1/1999 | Walter et al. | 623/16 |
| 6,001,352 A | 12/1999 | Boyan et al. | 424/93.7 |
| 6,630,142 B2 | 10/2003 | Hart et al. | 424/145.1 |
| 6,706,687 B1* | 3/2004 | Eriksson et al. | 514/12 |
| 2002/0164710 A1 | 11/2002 | Eriksson et al. | 435/69.1 |
| 2003/0073637 A1 | 4/2003 | Uutela et al. | 514/12 |
| 2003/0153495 A1* | 8/2003 | Lichenstein et al. | 514/12 |

FOREIGN PATENT DOCUMENTS

| | | |
|---|---|---|
| WO | WO91/005802 | 5/1991 |
| WO | WO91/018558 | 12/1991 |
| WO | WO93/000050 | 1/1993 |
| WO | WO93/020859 | 10/1993 |
| WO | WO00/027879 | 5/2000 |
| WO | WO00/034474 | 6/2000 |
| WO | WO01/025437 | 4/2001 |
| WO | WO01/055430 | 8/2001 |
| WO | WO01/089450 | 11/2001 |

OTHER PUBLICATIONS

Nash et al., *Bone* 15(2):203-208, 1994.

Canalis et al., Platelet-Derived Growth Factor and the Skeleton, *Principles of Bone Biology*, Academic Press, Inc., Chap. 44, 619-626, 1996.

Yu et al., *Am. J. Physiol.* 272(Cell Physiol. 41): C1709-C1716, 1997.

Howell et al., *J. Periodontal* 68(12):1186-1193, 1997.

Stephan et al., *J. Periodontal* 71(12):1887-1892, 2000.

* cited by examiner

METHODS FOR PROMOTING GROWTH OF BONE, LIGAMENT, AND CARTILAGE USING ZVEGF4

CROSS-REFERENCE TO RELATED APPLICATION

This application is a continuation of U.S. application Ser. No. 10/226,559, filed Aug. 23, 2002, now U.S. Pat. No. 6,866,991 incorporated herein by reference, which is a divisional of U.S. application Ser. No. 09/540,224, filed Mar. 31, 2000, now U.S. Pat. No. 6,468,543, incorporated herein by reference, which claims the benefit of U.S. Provisional Applications Ser. No. 60/132,250, filed May 3, 1999, Ser. No. 60/164,463, filed Nov. 10, 1999, and Ser. No. 60/180,169, filed Feb. 4, 2000.

BACKGROUND OF THE INVENTION

Bone remodeling is the dynamic process by which tissue mass and skeletal architecture are maintained. The process is a balance between bone resorption and bone formation, with two cell types, the osteoclast and osteoblast, thought to be the major players. Osteoblasts synthesize and deposit new bone into cavities that are excavated by osteoclasts. The activities of osteoblasts and osteoclasts are regulated by many factors, systemic and local, including growth factors.

Many of the proteins that influence the proliferation, differentiation, and activity of osteoblasts, osteoclasts, and their precursors also affect these processes in chondrocytes, the cells responsible for cartilage formation (chondrogenesis). These proteins include platelet-derived growth factor (PDGF), insulin-like growth factor (IGF), basic fibroblast growth factor (bFGF), transforming growth factor beta (TGF-β), bone morphogenetic proteins (BMP), and cartilage-derived growth factor (CDGF).

The exact mode by which PDGF affects the growth of osteoblasts is not yet clearly understood, however, this growth factor is generally believed to play a key role in the regulation of both normal skeletal remodeling and fracture repair. Biologically active PDGF is found as a homodimer or a heterodimer of the component A and B chains. In vitro studies have shown PDGF to be mitogenic for osteoblasts (Abdennagy et al., *Cell Biol. Internat. Rep.* 16(3):235–247, 1992). Mitogenic activity as well as chemotactic activities associated with PDGF have been demonstrated when the growth factor is added to normal osteoblast-like cells (Tuskamota et al. *Biochem. Biophys. Res. Comm.*, 175(3): 745–747, 1991) and primary osteoblast cultures (Centrella et al. *Endocrinol.* 125 (1):13–19, 1989). Recent studies have demonstrated that the osteoblast produces the AA isoform of PDGF (Zhang et al., *Am. J. Physiol.* 261:c348–c354, 1991).

PDGF has been shown to be useful for promoting the repair of both soft and hard tissues. For example, PDGF has been shown to promote the regeneration of bone and ligament in patients suffering from periodontal disease (Howell et al., *J. Periodontol.* 68:1186–1193, 1997). As disclosed in U.S. Pat. No. 5,533,836, PDGF stimulates the growth of osteoblasts, and this activity is enhanced in the presence of vitamin D. PDGF has also been shown to promote the healing of gastrointestinal ulcers (U.S. Pat. No. 5,234,908) and dermal ulcers (Robson et al., *Lancet* 339:23–25, 1992; Steed et al., *J. Vasc. Surg.* 21:71–81, 1995). The use of PDGF for stimulating chondrocyte proliferation and regenerating cartilage is disclosed in U.S. Pat. No. 6,001,352.

A PDGF homolog known as "zvegf3" was recently identified (U.S. patent application Ser. No. 09/457,066). This protein has also been designated "VEGF-R" (WIPO Publication WO 99/37671). A related protein, designated "zvegf4", has also been identified (U.S. patent application Ser. Nos. 09/304,216 and 60/132,250). Zvegf3 and zvegf4 are multi-domain proteins with significant homology to the PDGF/VEGF family of growth factors. WO 99/37671 discloses that VEGF-R is an angiogenic factor.

Despite the increasing knowledge of the role of growth factors in tissue growth and repair, there remains a need in the art for materials and methods for promoting the growth of bone, ligament, and cartilage. There also remains a need the art for materials and methods for modulating the proliferation and differentiation of cells in vitro and in vivo.

DESCRIPTION OF THE INVENTION

The present invention provides a method for promoting growth of bone, ligament, or cartilage in a mammal comprising administering to said mammal a composition comprising a pharmacologically effective amount of zvegf4 in combination with a pharmaceutically acceptable delivery vehicle. Within certain embodiments of the invention the delivery vehicle is powdered bone, tricalcium phosphate, hydroxyapatite, polymethacrylate, a biodegradable polyester, an aqueous polymeric gel, or a fibrin sealant. Within another embodiment of the invention the composition is locally administered at a site of a bony defect, such as a fracture, bone graft site, implant site, or periodontal pocket. Within another embodiment of the invention, the composition is administered systemically. Within a further embodiment of the invention, the zvegf4 is covalently linked to a bone-targetting agent. Within a further embodiment of the invention, the composition is locally administered at a joint. The composition may further comprise a protein selected from the group consisting of insulin-like growth factor 1, platelet-derived growth factor, epidermal growth factor, transforming growth factor-alpha, transforming growth factor-beta, a bone morphogenetic protein, parathyroid hormone, osteoprotegerin, or a fibroblast growth factor.

The invention also provides a method for promoting proliferation or differentiation of cells comprising culturing the cells in an effective amount of zvegf4, wherein the cells are osteoblasts, osteoclasts, chondrocytes, or bone marrow stem cells. Within one embodiment the cells are bone marrow stem cells, and the method comprises harvesting the bone marrow stem cells from a patient prior to culturing. Within other embodiments the method further comprises the step of recovering osteoblasts, osteoclasts, or chrodrocytes from the cultured cells.

The invention also provides a method for promoting cartilage growth comprising the steps of (a) culturing chondrocytes ex vivo in the presence of zvegf4 under conditions wherein the chondrocytes proliferate, and and (b) placing the cultured chondrocytes into a mammal where cartilage is to be grown. Within one embodiment the chondrocytes are placed into the mammal in association with a biodegradable matrix having sufficient porosity to permit cell ingrowth. Within a related embodiment the matrix comprises a protein selected from the group consisting of zvegf4, insulin-like growth factor 1, platelet-derived growth factor, epidermal growth factor, transforming growth factor-alpha, transforming growth factor-beta, a bone morphogenetic protein, parathyroid hormone, or a fibroblast growth factor.

BRIEF DESCRIPTION OF THE DRAWING

These and other aspects of the invention will become evident upon reference to the following detailed disclosure and the accompanying drawing. The drawings is a Hopp/ Woods hydrophilicity profile of the amino acid sequence shown in SEQ ID NO:2. The profile is based on a sliding six-residue window. Buried G, S, and T residues and exposed H, Y, and W residues were ignored. These residues are indicated in the figure by lower case letters.

As used herein, the term "bony defect" denotes a defect or void in a bone where restoration of the bone is desirable. Bony defects may arise from injury, surgery, tumor removal, ulceration, infection, or other causes, and include congenital defects. Examples of bony defects include fractures, voids resulting from tumor removal, and bone loss resulting from periodontal disease.

Figure 1A:
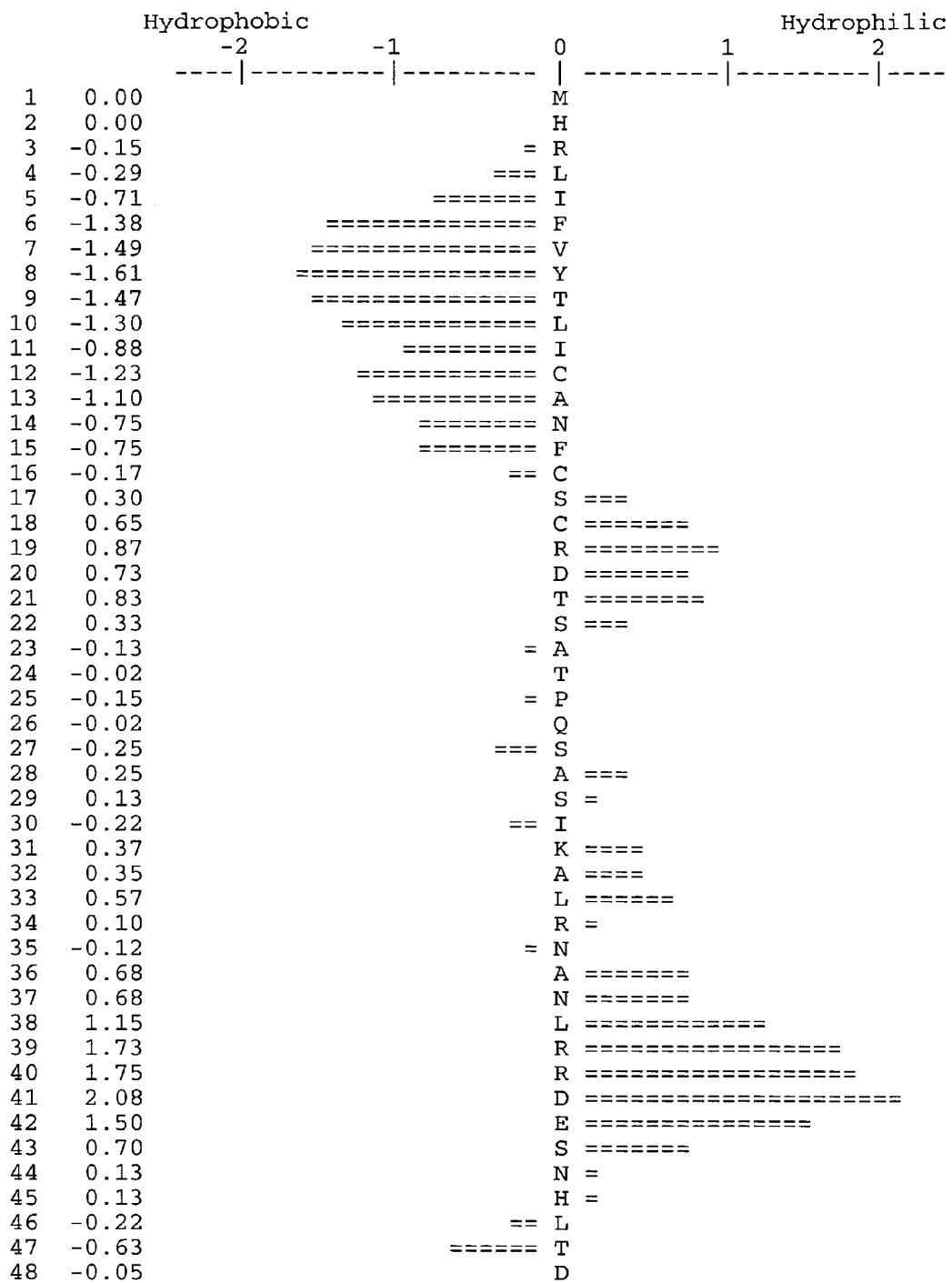
Figure 1H:
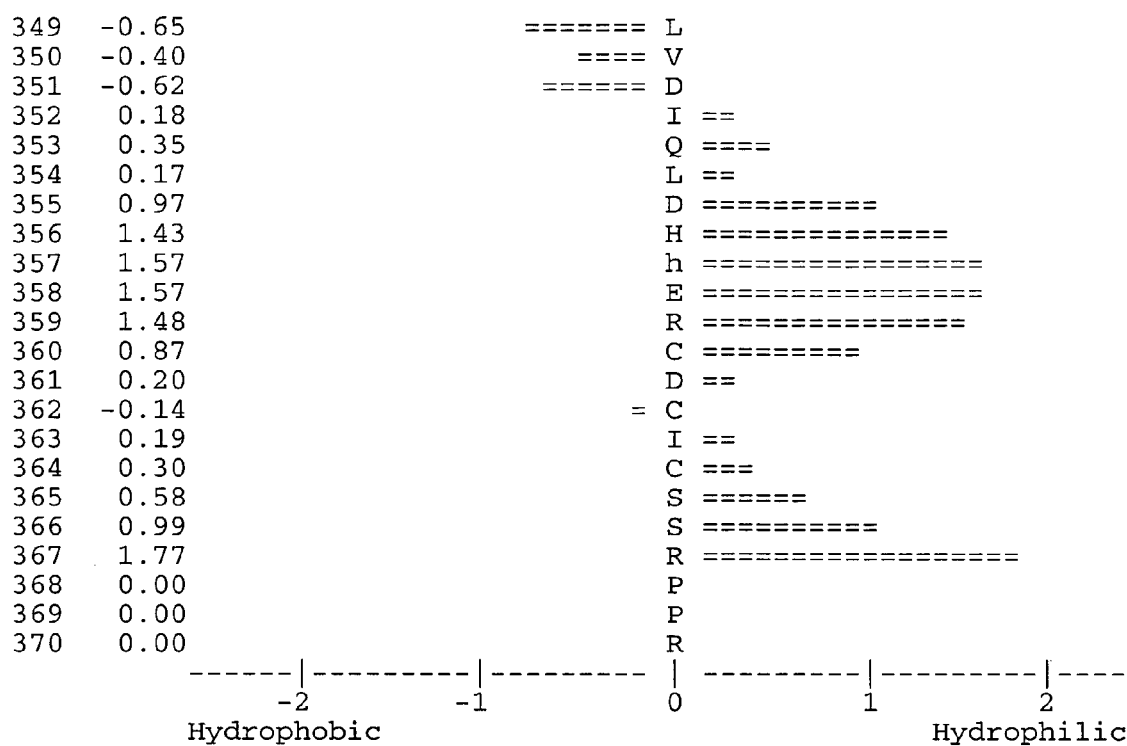

The terms "locally administered" and "local administration" are used to describe the application of a pharmaceutical agent at the intended site of action. Examples of local administration include, without limitation, injection into a joint space, implantation of a solid or semi-solid matrix, and direct application at a surgical site or wound. Local administration does not preclude the transmission of minor amounts of the agent to other parts of the body, such as by diffusion or circulation.

The term "zvegf4 protein" is used herein to denote proteins comprising a biologically active portion of a zvegf4 polypeptide (e.g., human zvegf4 as shown in SEQ ID NO:2 or mouse zvegf4 as shown in SEQ ID NO:4) that is mitogenic or chemotactic for mesenchymal cells. Experimental evidence indicates that biologically active zvegf4 is a dimeric protein. Zvegf4 proteins include homodimers and heterodimers as disclosed below. Using methods known in the art, zvegf4 proteins can be prepared in a variety of forms, including glycosylated or non-glycosylated; pegylated or non-pegylated; with or without an initial methionine residues; and as fusion proteins as disclosed in more detail below.

The present invention provides methods for promoting the growth of bone, connective tissue (including ligament, tendon, and cartilage), and related cell types using zvegf4 proteins. Zvegf4 is a protein that is structurally related to platelet-derived growth factor (PDGF) and the vascular endothelial growth factors (VEGF). The zvegf4 polypeptide chain comprises a growth factor domain and a CUB domain. The growth factor domain is characterized by an arrangement of cysteine residues and beta strands that is characteristic of the "cystine knot" structure of the PDGF family. The CUB domain shows sequence homology to CUB domains in the neuropilins (Takagi et al., Neuron 7:295–307, 1991; Soker et al., ibid.), human bone morphogenetic protein-1 (Wozney et al., Science 242:1528–1534, 1988), porcine seminal plasma protein and bovine acidic seminal fluid protein (Romero et al., Nat. Struct. Biol. 4:783–788, 1997), and X. laevis tolloid-like protein (Lin et al., Dev. Growth Differ. 39:43–51, 1997).

Structural predictions based on the zvegf4 sequence and its homology to other growth factors suggests that the polypeptide can form homomultimers or heteromultimers having growth factor activity, i.e., modulating one or more of cell proliferation, migration, differentiation, and metabolism. While not wishing to be bound by theory, the similarity of zvegf4 to other members of the PDGF/VEGF family suggests that zvegf4 may also form heteromultimers with other members of the family, including VEGF, VEGF-B, VEGF-C, VEGF-D, zvegf3 (SEQ ID NO:5), PlGF (Maglione et al., Proc. Natl. Acad. Sci. USA 88:9267–9271, 1991), PDGF-A (Murray et al., U.S. Pat. No. 4,899,919; Heldin et al., U.S. Pat. No. 5,219,759), or PDGF-B (Chiu et al., Cell 37:123–129, 1984; Johnsson et al., EMBO J. 3:921–928, 1984).

A representative human zvegf4 polypeptide sequence is shown in SEQ ID NO:2, and a representative mouse zvegf4 polypeptide sequence is shown in SEQ ID NO:4. DNAs encoding these polypeptides are shown in SEQ ID NOS:1 and 3, respectively. Analysis of the amino acid sequence shown in SEQ ID NO:2 indicates that residues 1 to 18 form a secretory peptide. The CUB domain extends from residue 52 to residue 179. A propeptide-like sequence extends from residue 180 to residue 257, and includes two potential cleavage sites at its carboxyl terminus, a dibasic site at residues 254–255 and a target site for furin or a furin-like protease at residues 254–257. The growth factor domain extends from residue 258 to residue 370. Those skilled in the art will recognize that domain boundaries are somewhat imprecise and can be expected to vary by up to ±5 residues from the specified positions. Processing of recombinant zvegf4 produced in a baculovirus expression system has been found to occur between residues 249 and 250. Signal peptide cleavage is predicted to occur after residue 18 (±3 residues), and cleavage after residue 34 has been observed in protein from the baculovirus system. This analysis suggests that the zvegf4 polypeptide chain may be cleaved to produce a plurality of monomeric species as shown in Table 1.

TABLE 1

| Monomer | Residues (SEQ ID NO: 2) |
|---|---|
| Cub domain | 19–179 |
| | 35–179 |
| | 52–179 |
| CUB domain + interdomain region | 19–257 |
| | 35–257 |
| | 52–257 |
| | 19–255 |
| | 35–255 |
| | 52–255 |
| | 19–253 |
| | 35–253 |
| | 52–253 |
| | 19–249 |
| | 35–249 |
| | 52–249 |
| Cub domain + interdomain region + growth factor domain | 19–370 |
| | 35–370 |
| | 52–370 |
| Growth factor domain | 250–370 |
| | 258–370 |
| Growth factor domain + interdomain region | 180–370 |

Zvegf4 can thus be prepared in a variety of multimeric forms comprising a zvegf4 polypeptide as disclosed above. Variants and derivatives of these polypeptides can also be prepared as disclosed herein.

Zvegf4 proteins can be prepared as fusion proteins comprising amino- or carboxyl-terminal extensions, such as an amino-terminal methionine residue, an affinity tag, or a targetting polypeptide. For example, a zvegf4 protein can be prepared as a fusion with an affinity tag to facilitate purification. In principal, any peptide or protein for which an antibody or other specific binding agent is available can be used as an affinity tag. Affinity tags include, for example, a poly-histidine tract, protein A (Nilsson et al., EMBO J. 4:1075, 1985; Nilsson et al., Methods Enzymol. 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–1210, 1988), streptavidin binding peptide, maltose binding protein (Guan et al., *Gene* 67:21–30, 1987), cellulose binding protein, thioredoxin, ubiquitin, T7 polymerase, or other antigenic epitope or binding domain. Fusion of zvegf4 to, for example, maltose binding protein or glutatione S transferase, can be used to improve yield in bacterial expression systems. In these instances the non-zvegf4 portion of the fusion protein ordinarily will be removed prior to use. Separation of the zvegf4 and non-zvegf4 portions of the fusion protein is facilitated by providing a specific cleavage site between the two portions. Such methods are well known in the art. Zvegf4 can also be fused to a targetting peptide, such as an antibody (including polyclonal antibodies, monoclonal antibodies, antigen-binding fragments thereof such as F(ab')$_2$ and Fab fragments, single chain antibodies, and the like), calcitonin, or other peptidic moiety that binds to bone or connective tissue.

Variations can be made in the zvegf4 amino acid sequences shown in SEQ ID NO:2 and SEQ ID NO:4. Such variations include amino acid substitutions, deletions, and insertions. Amino acid sequence changes are made in zvegf4 polypeptides so as to minimize disruption of higher order structure essential to biological activity. In general, conservative amino acid changes are preferred. Changes in amino acid residues will be made so as not to disrupt the cystine knot and "bow tie" arrangement of loops in the growth factor domain that is characteristic of the protein family. Conserved motifs will also be maintained. The effects of amino acid sequence changes can be predicted by computer modeling as disclosed above or determined by analysis of crystal structure (see, e.g., Lapthorn et al., *Nature* 369:455, 1994). A hydrophobicity profile of SEQ ID NO:2 is shown in the drawing. Those skilled in the art will recognize that this hydrophobicity will be taken into account when designing alterations in the amino acid sequence of a zvegf4 polypeptide, so as not to disrupt the overall profile. Additional guidance in selecting amino acid subsitutions is provided by a comparison of the mouse (SEQ ID NO:4) and human (SEQ ID NO:2) zvegf4 sequences. The amino acid sequence is highly conserved between mouse and human zvegf4s, with an overall amino acid sequence identity of 85.1%.

It is preferred that the sequence of a zvegf4 polypeptide be at least 95% identical to the corresponding region of SEQ ID NO:2 or SEQ ID NO:4. Percent sequence identity is determined by conventional methods. See, for example, Altschul et al., *Bull. Math. Bio.* 48:603–616, 1986, and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as:

$$\frac{\text{Total number of identical matches}}{[\text{length of the longer sequence plus the number of gaps introduced into the longer sequence in order to align the two sequences}]} \times 100$$

Zvegf4 proteins can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in *Xenopus* oocytes by microinjection of mutated mRNA and chemically aminoacylated suppressor tRNAs (Turcatti et al., *J. Biol. Chem.* 271:19991–19998, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

Essential amino acids in zvegf4 proteins can be identified according to procedures known in the art, such as site-directed mutagenesis or alanine-scanning mutagenesis (Cunningham and Wells, *Science* 244, 1081–1085, 1989; Bass et al., *Proc. Natl. Acad. Sci. USA* 88:4498–4502, 1991). Multiple amino acid substitutions can be made and tested using known methods of mutagenesis and screening, such as those disclosed by Reidhaar-Olson and Sauer (*Science* 241: 53–57, 1988) or Bowie and Sauer (*Proc. Natl. Acad. Sci. USA* 86:2152–2156, 1989). Other methods that can be used include phage display (e.g., Lowman et al., *Biochem.* 30:10832–10837, 1991; Ladner et al., U.S. Pat. No. 5,223, 409; Huse, WIPO Publication WO 92/06204), region-directed mutagenesis (Derbyshire et al., *Gene* 46:145, 1986; Ner et al., *DNA* 7:127, 1988), and DNA shuffling as disclosed by Stemmer (*Nature* 370:389–391, 1994) and Stemmer (*Proc. Natl. Acad. Sci. USA* 91:10747–10751, 1994). The resultant mutant molecules are tested for mitogenic activity or other properties (e.g., receptor binding) to identify amino acid residues that are critical to the activity of the molecule. Mutagenesis can be combined with high volume or high-throughput screening methods to detect biological activity of zvegf4 variant polypeptides, in particular biological activity in modulating cell proliferation or cell differentiation. For example, mitogenesis assays that measure dye incorporation or $^3$H-thymidine incorporation can be carried out on large numbers of samples.

Using the methods discussed above, one of ordinary skill in the art can identify and/or prepare a variety of polypeptides that are homologous to the zvegf4 polypeptides disclosed above in Table 1 and retain the biological properties of the wild-type protein.

Zvegf4 proteins for use within the present invention, including full-length polypeptides, biologically active fragments, and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms). Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al., eds., *Current Protocols in Molecular Biology,* Green and Wiley and Sons, NY, 1993.

In general, a DNA sequence encoding a zvegf4 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zvegf4 polypeptide into the secretory pathway of a host cell, a secretory signal sequence (also known as a leader sequence, prepro sequence or pre sequence) is provided in the expression vector. The secretory signal sequence may be that of zvegf4, or may be derived from another secreted protein (e.g., t-PA; see, U.S. Pat. No. 5,641,655) or synthesized de novo. The secretory signal sequence is operably linked to the zvegf4 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Expression of zvegf4 polypeptides via a host cell secretory pathway is expected to result in the production of multimeric proteins. As noted above, such multimers include both homomultimers and heteromultimers, the latter including proteins comprising only zvegf4 polypeptides and proteins including zvegf4 and heterologous polypeptides. For example, a heteromultimer comprising a zvegf4 polypeptide and a polypeptide from a related family member (e.g., VEGF, VEGF-B, VEGF-C, VEGF-D, zvegf3, PlGF, PDGF-A, or PDGF-B) can be produced by co-expression of the two polypeptides in a host cell. Sequences encoding these other family members are known. See, for example, Dvorak et al, ibid.; Olofsson et al, ibid.; Hayward et al., ibid.; Joukov et al., ibid.; Oliviero et al., ibid.; Achen et al., ibid.; Maglione et al., ibid.; Heldin et al., U.S. Pat. No. 5,219,759; and Johnsson et al., ibid. If a mixture of proteins results from expression, individual species are isolated by conventional methods. Monomers, dimers, and higher order multimers are separated by, for example, size exclusion chromatography. Heteromultimers can be separated from homomultimers by immunoaffinity chromatography using antibodies specific for individual dimers or by sequential immunoaffinity steps using antibodies specific for individual component polypeptides. See, in general, U.S. Pat. No. 5,094,941. Multimers may also be assembled in vitro upon incubation of component polypeptides under suitable conditions. In general, in vitro assembly will include incubating the protein mixture under denaturing and reducing conditions followed by refolding and reoxidation of the polypeptides to from homodimers and heterodimers. Recovery and assembly of proteins expressed in bacterial cells is disclosed below.

Zvegf4 proteins can be produced in eukaryotic host cells, including fungal cells (e.g., *Saccharomyces cerevisiae, Pichia methanolica,* and *Pichia pastoris*), mammalian cells, plant cells, and insect cells according to conventional methods. See, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; Murray et al., U.S. Pat. No. 4,845,075; Gleeson et al., *J. Gen. Microbiol.* 132:3459–3465, 1986; Cregg, U.S. Pat. No. 4,882,279; Raymond et al., *Yeast* 14:11–23, 1998; McKnight et al., U.S. Pat. No. 4,935,349; Sumino et al., U.S. Pat. No. 5,162,228; Lambowitz, U.S. Pat. No. 4,486,533; Raymond et al., U.S. Pat. No. 5,854,039; Raymond, U.S. Pat. Nos. 5,716,808, 5,736,383, and 5,888,768; Levinson et al., U.S. Pat. No. 4,713,339; Hagen et al., U.S. Pat. No. 4,784,950; Palmiter et al., U.S. Pat. No. 4,579,821; Foster et al., U.S. Pat. No. 4,959,318; Mulvihill et al., U.S. Pat. No. 5,648,254; Moore et al., U.S. Pat. No. 5,622,839; Kuestner et al., U.S. Pat. No. 6,008,322; Sinkar et al., *J. Biosci. (Bangalore)* 11:47–58, 1987; Luckow et al., *J. Virol.* 67:4566–4579, 1993; Hill-Perkins and Possee, *J. Gen. Virol.* 71:971–976, 1990; Bonning et al., *J. Gen. Virol.* 75:1551–1556, 1994; and Chazenbalk and Rapoport, *J. Biol. Chem.* 270:1543–1549, 1995. Suitable host strain and cell lines are known in the art and available from public depositories such as the American Type Culture Collection, Manassas, Va., USA. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Expression vectors for use in mammalian cells include pZP-1 and pZP-9, which have been deposited with the American Type Culture Collection, Manassas, Va., USA under accession numbers 98669 and 98668, respectively. Cells, expression vectors, expression kits, and other materials are available from commercial suppliers.

Prokaryotic host cells, including strains of the bacteria *Escherichia coli, Bacillus* and other genera can also be used for production of zvegf4 proteins. Techniques for transforming these hosts and expressing foreign DNA sequences cloned therein are well known in the art (see, e.g., Sambrook et al., ibid.). When expressing a zvegf4 polypeptide in bacteria such as *E. coli,* the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted polypeptides can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Zvegf4 polypeptides or fragments thereof can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989.

Covalent complexes can also be made by isolating the desired component polypeptides and combining them in vitro. Covalent complexes that can be prepared in this manner include homodimers of zvegf4 polypeptides, heterodimers of two different zvegf4 polypeptides, and heterodimers of a zvegf4 polypeptide and a polypeptide from another family member of the VEGF/PDGF family of proteins. The two polypeptides are mixed together under denaturing and reducing conditions, followed by renaturation of the proteins by removal of the denaturants. Removal can be done by, for example, dialysis or size exclusion chromatography to provide for buffer exchange. When combining two different polypeptides, the resulting renatured proteins may form homodimers of the individual components as well as heterodimers of the two polypeptide components. See, Cao et al., *J. Biol. Chem.* 271:3154–3162, 1996.

Zvegf4 proteins are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321–1325, 1988. Proteins comprising a glu-glu tag can be purified by immunoaffinity chromatography according to conventional procedures. See, for example, Grussenmeyer et al., ibid. Maltose binding protein fusions are purified on an amylose column according to methods known in the art.

Zvegf4 proteins can be used wherever it is desired to stimulate the production of bone and/or connective tissue in both humans and non-human animals. Veterinary uses include use in domestic animals, including livestock and companion animals. Specific applications include, without limitation, fractures, including non-union fractures and fractures in patients with compromised healing, such as diabetics, alcoholics, and the aged; bone grafts; healing bone following radiation-induced osteonecrosis; implants, including joint replacements and dental implants; repair of bony defects arising from surgery, such as cranio-maxilofacial repair following tumor removal, surgical reconstruction following tramatic injury, repair of hereditary or other physical abnormalities, and promotion of bone healing in plastic surgery; treatment of periodontal disease and repair of other dental defects; treatment of bone defects following therapeutic treatment of bone cancers; increase in bone formation during distraction osteogenesis; treatment of joint injuries, including repair of cartilage and ligament; repair of joints that have been afflicted with osteoarthritis; tendon repair and re-attachment; treatment of osteoporosis (including age-related osteoporosis, post-menopausal osteoporosis, glutocorticoid-induced osteoporosis, and disuse osteoporosis) and and other conditions characterized by increased bone loss or decreased bone formation; elevation of peak bone mass in pre-menopausal women; and use in the healing of connective tissues associated with dura mater.

For use within the present invention, zvegf4 proteins are formulated for local or systemic (particularly intravenous or subcutaneous) delivery according to conventional methods. In general, pharmaceutical formulations will include a zvegf4 protein in combination with a pharmaceutically acceptable delivery vehicle. Delivery vehicles include biocompatible solid or semi-solid matrices, including powdered bone, ceramics, biodegradable and non-biodegradable synthetic polymers, and natural polymers; tissue adhesives (e.g., fibrin-based); aqueous polymeric gels; aqueous solutions; liposomes; and the like. Exemplary formulations and delivery vehicles are disclosed below. This disclosure is illustrative; those skilled in the art will readily recognize suitable alternatives, including derivatives of the specifically named materials and combinations of materials. Formulations may further include one or more additional growth factors, excipients, preservatives, solubilizers, buffering agents, albumin to prevent protein loss on vial surfaces, etc. Methods of formulation are well known in the art and are disclosed, for example, in *Remington: The Science and Practice of Pharmacy*, Gennaro, ed., Mack Publishing Co., Easton, Pa., 19th ed., 1995. An "effective amount" of a composition is that amount that produces a statistically significant effect, such as a statistically significant increase in the rate of fracture repair, reversal of bone loss in osteoporosis, increase in the rate of healing of a joint injury, increase in the reversal of cartilage defects, increase or acceleration of bone growth into prosthetic devices, improved repair of dental defects, and the like. The exact dose will be determined by the clinician according to accepted standards, taking into account the nature and severity of the condition to be treated, patient traits, etc. Determination of dose is within the level of ordinary skill in the art. Depending upon the route and method of administration, the protein may be administered in a single dose, as a prolonged infusion, or intermittently over an extended period. Intravenous administration will be by bolus injection or infusion over a typical period of one to several hours. Sustained release formulations can be employed. In general, a therapeutically effective amount of zvegf4 is an amount sufficient to produce a clinically significant change in the treated condition, such as a clinically significant reduction in time required for fracture repair, a significant reduction in the volume of a void or other defect, a significant increase in bone density, a significant reduction in morbidity, or a significantly increased histological score.

Zvegf4 will ordinarily be used in a concentration of about 10 to 100 µg/ml of total volume, although concentrations in the range of 1 ng/ml to 1000 µg/ml may be used. For local application, such as for the regeneration of bone in a fracture or other bony defect, the protein will be applied in the range of 0.1–100 µg/cm$^2$ of wound area.

Within the present invention zvegf4 can be used in combination with other growth factors and other therapeutic agents that have a positive effect on the growth of bone or connective tissue. Such growth factors include insulin-like growth factor 1 (IGF-1), PDGF, alpha and beta transforming growth factors (TGF-α and TGF-β), epidermal growth factor (EGF), bone morphogenetic proteins, leukemia inhibitory factor, and fibroblast growth factors. Other therapeutic agents include vitamin D, bisphosphonates, calcitonin, estrogens, parathyroid hormone, osteogenin, NaF, osteoprotegerin, and statins.

Zvegf4 can be delivered as a component of a tissue adhesive. Fibrin-based tissue adhesives are known in the art, and can be prepared from plasma or recombinant sources. Tissue adhesives comprise fibrinogen and factor XIII to which thrombin is added immediately before use to activate cross-linking. See, for example, Schwarz et al., U.S. Pat. No. 4,414,976; Stroetmann et al., U.S. Pat. No. 4,427,650; and Rose et al., U.S. Pat. No. 4,928,603. The use of tissue adhesives may be particularly advantageous in the treatment of conditions where connective tissue must be repaired, such as torn ligaments or tendons.

Solid and semisolid matrices are preferred delivery vehicles for filling non-union fractures, cavities, and other bony defects. These matrices provide a space-filling substitute for the natural bone, and include bone substituting agents such as tricalcium phosphate, hydroxyapatite, combinations of tricalcium phosphate and hydroxyapatite, polymethylmethacrylate, aluminates and other ceramics, and demineralized freeze-dried cortical bone. Solid and semisolid matrices can also be prepared from a variety of polymeric materials. Semi-solid matrices provide the advantage of maleability such that they can be shaped to provide a precise filling of a bony defect. Matrices may include other active or inert components. Of particular interest are those agents that promote tissue growth or infiltration. Agents that promote bone growth include bone morphogenic proteins (U.S. Pat. No. 4,761,471; PCT Publication WO 90/11366), osteogenin (Sampath et al., *Proc. Natl. Acad. Sci. USA* 84: 7109–7113, 1987), and NaF (Tencer et al., *J. Biomed. Mat. Res.* 23: 571–589, 1989).

Biodegradable, synthetic polymers include polyesters, polyorthoesters, polyanhydrides, polycarbonates, polyfumarates, polyhydroxybutyrate, vinyl polymers, and the like. Specific examples include, without limitation, polylactide, polyglycolide, polylactide/polyglycolide copolymers, polydioxanone, polyglycolide/trimethylene carbonate copolymers, polyacrylic acid, polymethacrylic acid, polyvinyl pyrrolidone, and polyvinyl alcohol. Such materials can be prepared in a variety shapes, including films, plates, pins, rods, screws, blocks, lattices, and the like for attachment to or insertion into bone. See, for example, Walter et al., U.S. Pat. No. 5,863,297; and WIPO publication WO 93/20859. These materials may further include a carrier such as albumin, a polyoxyethylenesorbitan detergent or glutamic acid.

In principle, any substance that enhances polymer degradation, creates pores in the matrix or reduces adsorption of the growth factor(s) to the matrix can be used as a carrier. Polyoxyethylenesorbitan detergents that are useful as carriers include polyoxyethylenesorbitan monooleate, polyoxyethylenesorbitan monolaureate, polyoxyethylenesorbitan monopalmitate, polyoxy-ethylenesorbitan monostearate and polyoxyethylenesorbitan trioleate. Plasticizers can also be included.

In general, a film or device as described herein is applied to the bone at a site of injury. Application is generally by implantation into the bone or attachment to the surface using standard surgical procedures.

Biodegradable polymer films are particularly useful as coatings for prosthetic devices and surgical implants. Such films can, for example, be wrapped around the outer surfaces of surgical screws, rods, pins, plates and the like, or can themselves be rolled or otherwise formed into a variety of shapes. Implantable devices of this type are routinely used in orthopedic surgery. Films can also be used to coat bone filling materials, such as hydroxyapatite blocks, demineralized bone matrix plugs, collagen matrices, and the like.

As used herein the term "copolymer" includes any polymer containing two or more types of monomer unit. Copolymers can be classified in four types as shown in the following chart, wherein "A" and "B" denote the component monomer units:

| | |
|---|---|
| Random: | -A-B-A-A-B-A-B-B-B-A-A-B- |
| Alternating: | -A-B-A-B-A-B-A-B-A-B-A-B- |
| Block: | -A-A-A-A-A-B-B-B-B-B-A-A- |
| Graft: | -A-A-A-A-A-A-A-A-A-A-A-A- |
| |     B    B |
| |     B    B |
| |     B    B |

Degradation of the matrix and consequent release of growth factors therefrom can be modulated by adjusting such parameters as molecular weight, copolymer structure, copolymer ratio, matrix thickness, and porosity, and by including a carrier as disclosed above. PLA/PGA films, for example, are generally formulated to provide a ratio of PLA:PGA between 75:25 and 25:75, more commonly between 65:35 and 35:65. In general, an implant will be prepared using a copolymer having a molecular weight between 10,000 and 200,000 Daltons. In general, lower molecular weight copolymers will degrade more rapidly than higher molecular weight formulations; random copolymers are less crystalline and therefore degrade more quickly than other types of copolymers; and polymers of enantiomeric lactides are crystalline and therefore more resistant to degradation than their racemic counterparts.

Polymer matrices are prepared according to procedures known in the art. See, for example, Loomis et al., U.S. Pat. No. 4,902,515; Gilding and Reed, *Polymer* 20: 1459–1464, 1979; and Boswell et al., U.S. Pat. No. 3,773,919. For example, PLA/PGA copolymer implants are produced by combining the desired amount of PLA/PGA copolymer granules in a suitable solvent (e.g., chloroform or methylene chloride), pouring the resulting solution into a mold, and completely evaporating the solvent. In the alternative, PLA/PGA implants can be produced by compression molding, extrusion, or other known methods. To load the matrix, zvegf4 and a carrier are applied as powders or liquid solutions. For example, lyophilized zvegf4 and albumin may be uniformly dispersed over one surface of polymer film, and the film folded over. By repeated this process, a multi-layered "sandwich" of polymer and growth factor can be constructed. In the alternative, the proteins can be applied as aqueous solutions (e.g., in phosphate buffered saline or 0.1 M acetic acid), which are allowed to dry. Porous implants can be soaked in a solution of zvegf4 (optionally containing other components), and the liquid evaporated. Zvegf4 can be worked into a maleable polymeric matrix after which the matrix is formed into the desired shape and cured at elevated temperature (e.g., 60–65° C.). Porous implants can be prepared by curing the matrix under vacuum.

Zvegf4 can also be delivered in combination with a biodegradable sponge, for example a gelatin, collagen, cellulose, or chitin sponge. Such sponges are known in the art. See, for example, Correll, U.S. Pat. No. 2,465,357; Miyata et al., U.S. Pat. No. 4,271,070; and Munck et al., WO 90/13320. A solution of zvegf4 and, optionally, one or more additional therapeutic agents is injected into the sponge, and the sponge is air-dried at a temperature of 30–100° C. for a time sufficient to reduce the water content to below 50%, preferably below 10%.

Gels can also be used as delivery vehicles. The use of aqueous, polymeric gels for the delivery of growth factors is disclosed by, for example, Finkenaur et al., U.S. Pat. No. 5,427,778; Edwards et al., U.S. Pat. No. 5,770,228; and Finkenaur et al., U.S. Pat. No. 4,717,717; and Cini et al., U.S. Pat. No. 5,457,093. Gels comprise biocompatible, water soluble or water swellable polymers that form viscous solutions in water. Such polymers include, without limitation, polysaccharides, including methyl cellulose, hydroxypropyl cellulose, hydroxypropylmethyl cellulose, hydroxyethyl cellulose, dextrans, starch, chitosan, and alginic acid; glycosaminoglycans, including hyaluronic acid, chondroitin, chondroitin sulfates, heparin, and heparan sulfate; proteins, including collagen, gelatin, and fibronectin; and acrylamides, including polyacrylamide and polymethacrylamide. Gels are generally prepared with a viscosity of from 200 cps to 100,000 cps, more commonly about 1000 cps to 30,000 cps at room temperature, the latter range corresponding to about 0.25–10% hydroxyethyl cellulose in water. Higher viscosity gels are known in the art (e.g., Finkenaur et al., U.S. Pat. No. 5,427,778). Viscosity can be adjusted by varying the concentration and/or length of the component polymer(s). Gels are prepared by combining the polymer with a suitable buffer, such as a low ionic strength citrate, phosphate, or acetate buffer at neutral or slightly acidic pH. A preservative (antimicrobial agent) such as methyl paraben, propyl paraben, benzyl alcohol, or the like, will generally be included. Following thorough mixing, the solution is sterilized by suitable means (e.g., autoclaving). The mixture is cooled, and filter-sterilized zvegf4 is added.

Alternative means for local delivery of zvegf4 include osmotic minipumps (e.g., ALZET® minipumps; Alza Corporation, Mountain View, Calif.); electrically charged dextran beads as disclosed in Bao et al. (WO 92/03125); collagen-based delivery systems, such as disclosed in Ksander et al. (*Ann. Surg.* 211:288–294, 1990); and alginate-based systems as disclosed in Edelman et al. (*Biomaterials,* 12:619–626, 1991). Other methods known in the art for sustained local delivery in bone include porous coated metal protheses that can be impregnated with a therapeutic agent and solid plastic rods with therapeutic compositions incorporated within them.

Zvegf4 can be further used to treat osteoporosis by administering a therapeutically effective amount of zvegf4 to an individual. Zvegf4 proteins can be further tested in known animal models using an in vivo dosing assay. Prototypical dosing may be accomplished by subcutaneous, intraperitoneal or oral administration, and may be performed by injection, sustained release or other delivery techniques. The time period for administration of avegf4 may vary (for instance, 28 days as well as 35 days may be appropriate).

Delivery of systemically adminstered compositions of the present invention may be enhanced by conjugating zvegf4 to a targeting molecule. A "targeting molecule" is a molecule that binds to the tissue of interest. For example, bone-targeting molecules include tetracyclines, calcein, bisphosphonates, polyaspartic acid, polyglutamic acid, aminophosphosugars, peptides known to be associated with the mineral phase of bone (e.g., osteonectin, bone sialoprotein, and osteopontin), bone-specific antibodies, proteins with bone mineral or bone cell binding domains (e.g., calcitonin), and the like. See, for example, the disclosures of Bentz et al., EP 512,844; Murakami et al., EP 341,961; and Brinkley, *Bioconjugate Chem.* 3:2–13, 1992. Conjugation will ordinarily be achieved through a covalent linkage, the precise nature of which will be determined by the targetting molecule and the linking site on the zvegf4 polypeptide. Typically, a non-peptidic agent is modified by the addition of a linker that allows conjugation to zvegf4 through its amino acid side chains, carbohydrate chains, or reactive groups introduced on zvegf4 by chemical modification. For example, a drug may be attached through the $\epsilon$-amino group of a lysine residue, through a free $\alpha$-amino group, by disulfide exchange to a cysteine residue, or by oxidation of the 1,2-diols in a carbohydrate chain with periodic acid to allow attachment of drugs containing various nucleophiles through a Schiff-base linkage. See, for example, Ali et al., U.S. Pat. No. 4,256,833. Protein modifying agents include amine-reactive reagents (e.g., reactive esters, isothiocyantates, aldehydes, and sulfonyl halides), thiol-reactive reagents (e.g., haloacetyl derivatives and maleimides), and carboxylic acid- and aldehyde-reactive reagents. Zvegf4 polypeptides can be covalently joined to peptidic agents through the use of bifunctional cross-linking reagents. Heterobifunctional reagents are more commonly used and permit the controlled coupling of two different proteins through the use of two different reactive moieties (e.g., amine-reactive plus thiol, iodoacetamide, or maleimide). The use of such linking agents is well known in the art. See, for example, Brinkley (ibid.) and Rodwell et al., U.S. Pat. No. 4,671,958. Peptidic linkers can also be employed. In the alternative, a zvegf4 polypeptide can be linked to a peptidic moiety through preparation of a fusion polypeptide.

Zvegf4 can be implanted in a mammalian body so that the zvegf4 is in contact with osteoblasts such that osteoblast proliferation occurs and bone growth is stimulated. For example, zvegf4 can be placed in a matrix in association with a bone morphogenic protein (BMP). The BMP induces the migration of mesenchymal osteoblast precursors to the site and further induces differentiation of the mesenchymal cells into osteoblasts. Zvegf4 will then stimulate the further proliferation of the osteoblasts. A suitable matrix is made up of particles of porous materials. The pores must be of a dimension to permit progenitor cell migration and subsequent differentiation and proliferation, generally in the range of 70–850 μm, commonly from 150 μm to 420 μm. The matrix containing the zvegf4 can be molded into a shape encompassing a bone defect. Examples of matrix materials are particulate, demineralized, guanidine extracted, species-specific bone. Other potentially useful matrix materials include collagen, homopolymers and copolymers of glycolic acid and lactic acid, hydroxyapatite, tricalcium phosphate and other calcium phosphates. Zvegf4 can be applied into a matrix at a sufficient concentration to promote the proliferation of osteoblasts, preferably at a concentration of at least 1 µg/ml of matrix. A solution of zvegf4 can also be injected directly into the site of a bone fracture to expedite healing of the fracture. Examples of BMPs and the use of matrices to produce are disclosed in PCT application publication number WO 92/07073, publication No. WO 91/05802, U.S Pat. No. 5,645,591 and U.S. Pat. No. 5,108,753.

As stated above, zvegf4 may also be used to promote the production of cartilage through its ability to stimulate the development or proliferation of chondrocytes. Zvegf4 can be injected directly into the site where cartilage is to be grown. For example, zvegf4 can be injected directly in joints which have been afflicted with osteoarthritis or other injured joints in which the cartilage has been worn down or damaged by trauma. In the alternative, zvegf4 can be deliverd in a suitable solid or semi-solid matrix as disclosed above.

Cartilage can also be grown by first removing chondrocytes from a patient and culturing them in the presence of zvegf4 so that they proliferate. Chondrocytes are cultured for from several hours to a day or longer according to conventional methods in a culture medium (e.g., DMEM supplemented with 10% patient's serum) containing from about 0.1 µg/ml to about 100 µg/ml zvegf4. The proliferated chondrocytes are reimplanted into the patient where cartilage needs to be produced. The proliferated chondrocytes can be delivered in a porous matrix having sufficient porosity to permit cell ingrowth as generally disclosed above. Additional zvegf4 can be included in the matrix to promote further chondrocyte proliferation after implantation. See, in general, Walter et al., U.S. Pat. No. 5,863,297 and Boyan et al., U.S. Pat. No. 6,001,352.

Within another embodiment, the present invention provides methods for stimulating the growth and/or differentiation of bone-forming and cartilage-forming cells, or their precursors, in vitro. Using these methods, cells can be harvested from a patient, expanded ex vivo, and returned to the patient as generally disclosed above. Of particular interest is the growth and/or differentiation of bone marrow cells, which can be cultured in the presence of differentiation-stimulating agents to develop into, inter alia, osteoblasts, osteoclasts, and chondrocytes. Identification of differentiated cells within a primary culture is primarily phenotypic. For example, the phenotypic markers for osteoblasts include expression of alkaline phosphatase (Manduca et al., *J. Bone Min. Res.* 8:281, 1993), type 1 collagen synthesis (Kurihara et al., *Endocrinol.* 118(3):940–947, 1986), production of osteocalcin (Yoon et al., *Biochem.* 27:8521–8526, 1988) and responsiveness to parathyroid hormone (Aubin et al., *J. Cell Biol.*, 92:452–461, 1982). Osteoblast cells are typically cultured at 37° C. in 5% $CO_2$ in a growth medium that includes a carbon source, a nitrogen source, essential amino acids, vitamins, minerals and growth factors generally supplied by fetal calf serum. A variety of suitable media are known in the art. Zvegf4 polypeptides are added to tissue culture media for these cell types at a concentration of about 10 pg/ml to about 1000 ng/ml. Those skilled in the art will recognize that zvegf4 proteins can be advantageously combined with other growth factors in culture media.

Bony defects or connective tissue injuries may also be repaired using a gene therapy approach wherein a polynucleotide encoding zvegf4 is administered to a patient. Gene delivery systems useful in this regard include adenovirus, adeno-associated virus, and naked DNA vectors. See, for example, by Anderson et al., U.S. Pat. No. 5,399,346; Mann et al., *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; Dougherty et al., WIPO publication WO 95/07358; and Kuo et al., *Blood* 82:845, 1993. Of particular interest is local infection of the affected tissue, such as local application of the vector to a periodontal pocket, fracture, joint, implant site, or site of prosthetic attachment.

The invention is further illustrated by the following, non-limiting examples.

EXAMPLE 1

An expression plasmid containing all or part of a polynucleotide encoding zvegf4 is constructed via homologous recombination. A fragment of zvegf4 cDNA is isolated by PCR using the polynucleotide sequence of SEQ ID NO: 1 with flanking regions at the 5' and 3' ends corresponding to the vector sequences flanking the zvegf4 insertion point. The primers for PCR each include from 5' to 3' end: 40 bp of flanking sequence from the vector and 17 bp corresponding to the amino and carboxyl termini from the open reading frame of zvegf4.

Ten µl of the 100 µl PCR reaction is run on a 0.8% LMP agarose gel (Seaplaque GTG) with 1×TBE buffer for analysis. The remaining 90 µl of PCR reaction is precipitated with the addition of 5 µl 1 M NaCl and 250 µl of absolute ethanol. The plasmid pZMP6, which has been cut with SmaI, is used for recombination with the PCR fragment. Plasmid pZMP6 was constructed from pZP9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain. pZMP6 is a mammalian expression vector containing an expression cassette having the mouse metallothionein-1 promoter, multiple restriction sites for insertion of coding sequences, a stop codon, and a human growth hormone terminator. The plasmid also contains an *E. coli* origin of replication; a mammalian selectable marker expression unit comprising an SV40 promoter, enhancer and origin of replication, a DHFR gene, and the SV40 terminator; as well as the URA3 and CEN-ARS sequences required for selection and replication in *S. cerevisiae*.

One hundred microliters of competent yeast cells (*S. cerevisiae*) are independently combined with 10 µl of the various DNA mixtures from above and transferred to a 0.2-cm electroporation cuvette. The yeast/DNA mixtures are electropulsed at 0.75 kV (5 kV/cm), ∞ ohms, 25 µF. To each cuvette is added 600 µl of 1.2 M sorbitol, and the yeast is plated in two 300-µl aliquots onto two URA-D plates and incubated at 30° C. After about 48 hours, the Ura$^+$ yeast transformants from a single plate are resuspended in 1 ml $H_2O$ and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 µl acid-washed glass beads and 200 µl phenol-chloroform, vortexed for 1 minute intervals two or three times, and spun for 5 minutes in an Eppendorf centrifuge at maximum speed. Three hundred microliters of the aqueous phase is transferred to a fresh tube, and the DNA is precipitated with 600 µl ethanol (EtOH), followed by centrifugation for 10 minutes at 4° C. The DNA pellet is resuspended in 10 µl H₂O.

Transformation of electrocompetent *E. coli* host cells (Electromax DH10B™ cells; obtained from Life Technologies, Inc., Gaithersburg, Md.) is done with 0.5–2 ml yeast DNA prep and 40 µl of cells. The cells are electropulsed at 1.7 kV, 25 µF, and 400 ohms. Following electroporation, 1 ml SOC (2% BACTO™ Tryptone (Difco, Detroit, Mich.), 0.5% yeast extract (Difco), 10 mM NaCl, 2.5 mM KCl, 10 mM MgCl₂, 10 mM MgSO₄, 20 mM glucose) is plated in 250-µl aliquots on four LB AMP plates (LB broth (Lennox), 1.8% BACTO™ Agar (Difco), 100 mg/L Ampicillin).

Individual clones harboring the correct expression construct for zvegf4 are identified by restriction digest to verify the presence of the zvegf4 insert and to confirm that the various DNA sequences have been joined correctly to one another. The inserts of positive clones are subjected to sequence analysis. Larger scale plasmid DNA is isolated using a commercially available kit (QIAGEN Plasmid Maxi Kit, Qiagen, Valencia, Calif.) according to manufacturer's instructions. The correct construct is designated zvegf4/pZMP6.

EXAMPLE 2

Recombinant zvegf4 having a carboxyl-terminal Glu-Glu affinity tag was produced in a baculovirus expression system according to conventional methods. The culture was harvested, and the cells were lysed with a solution of 0.02 M Tris-HCl, pH 8.3, 1 mM EDTA, 1 mM DTT, 1 mM 4-(2-Aminoethyl)-benzenesulfonyl fluoride hydrochloride (PEFABLOC® SC; Boehringer-Mannheim), 0.5 µM aprotinin, 4 mM leupeptin, 4 mM E-64, 1% NP-40 at 4° C. for 15 minutes on a rotator. The solution was centrifuged, and the supernatant was recovered. Twenty ml of extract was combined with 50 µl of anti-Glu-Glu antibody conjugated to cross-linked agarose (SEPHAROSE™) beads in 50 µl buffer. The mixture was incubated on a rotator at 4° C. overnight. The beads were recovered by centrifugation and washed 3×15 minutes at 4° C. Pellets were combined with sample buffer containing reducing agent and heated at 98° C. for five minutes. The protein was analyzed by polyacrylamide gel electrophoresis under reducing conditions followed by western blotting on a PVDF membrane using an antibody to the affinity tag. Two bands were detected, one a $M_r \approx 49$ kD and the other at $M_r \approx 21$ kD. Sequence analysis showed the larger band to comprise two sequences, one beginning at Arg-19 of SEQ ID NO:2 and the other beginning at Asn-35 of SEQ ID NO:2. The asparagine residue appeared to have been deamidated to an aspartic acid. The smaller band began at Ser-250 of SEQ ID NO:2.

EXAMPLE 3

Recombinant carboxyl-terminal Glu-Glu tagged zvegf4 (zvegf4-cee) was produced from recombinant baculovirus-infected insect cells. Two-liter cultures were harvested, and the media were sterile-filtered using a 0.2 µm filter.

Protein was purified from the conditioned media by a combination of anti-Glu-Glu (anti-EE) peptide antibody affinity chromatography and S-200 gel exclusion chromatography. Culture media (pH 6.0, conductivity 7 mS) was directly loaded onto a 20×80 mm (25-ml bed volume) anti-EE antibody affinity column at a flow of 6 ml/minute. The column was washed with ten column volumes of PBS, then bound protein was eluted with two column volumes of 0.4 mg/ml EYMPTD peptide (SEQ ID NO:6) (Princeton BioMolecules Corp., Langhorne, Pa.). Five-ml fractions were collected. Samples from the anti-EE antibody affinity column were analyzed by SDS-PAGE with silver staining and western blotting (as disclosed below) for the presence of zvegf4-cee. Zvefg4-cee-containing fractions were pooled and concentrated to 3.8 ml by filtration using a BIOMAX™-5 concentrator (Millipore Corp., Bedford, Mass.), and loaded onto a 16×1000 mm gel filtration column (SEPHACRYL™ S-200 HR; Amersham Pharmacia Biotech, Piscataway, N.J.). The fractions containing purified zvegf4-cee were pooled, filtered through a 0.2 µm filter, aliquoted into 100 µl each, and frozen at −80° C. The concentration of the final purified protein was determined by colorimetric assay (BCA assay reagents; Pierce, Rockford, Ill.) and HPLC-amino acid analysis.

Recombinant zvegf4-cee was analyzed by SDS-PAGE (NUPAGE™ 4–12% gel; Novex, San Diego, Calif.) with silver staining (FASTSILVER™, Geno Technology, Inc., Maplewood, Mo.) and Western blotting using rabbit polyclonal antibodies to peptides huzvegf4-1 (CGHKEVPPRIK-SRTNQIK; SEQ ID NO:7), huzvegf4-2 (ESWQEDLEN-MYLDTPRYRGRSYHDC; SEQ ID NO:8), huzvegf4-3 (CFEPGHIKRRGRAKTMALVDIQLD; SEQ ID NO:9), and anti-EE antibody. Either the conditioned media or purified protein was electrophoresed using an electrophoresis 2 0 mini-cell (XCELL II™ mini-cell; Novex, San Diego, Calif.) and transferred to nitrocellulose (0.2 µm; Bio-Rad Laboratories, Hercules, Calif.) at room temperature using an XCELL II™ blot module (Novex) with stirring according to directions provided in the instrument manual. The transfer was run at 500 mA for one hour in a buffer containing 25 mM Tris base, 200 mM glycine, and 20% methanol. The filters were then blocked with 10% non-fat dry milk in PBS for 10 minutes at room temperature. The nitrocellulose was quickly rinsed, then primary antibody was added in PBS containing 2.5% non-fat dry milk. The blots were incubated for two hours at room temperature or overnight at 4° C. with gentle shaking. Following the incubation, blots were washed three times for 10 minutes each in PBS. Secondary antibody (goat anti-rabbit IgG conjugated to horseradish peroxidase; obtained from Rockland Inc., Gilbertsville, Pa.) diluted 1:2000 in PBS containing 2.5% non-fat dry milk was added, and the blots were incubated for two hours at room temperature with gentle shaking. The blots were then washed three times, 10 minutes each, in PBS, then quickly rinsed in H₂O. The blots were developed using commercially available chemiluminescent substrate reagents (SUPERSIGNAL® ULTRA reagents 1 and 2 mixed 1:1; reagents obtained from Pierce), and the signal was captured using image analysis software (LUMI-IMAGER™ Lumi Analyst 3.0; Roche Molecular Biochemicals, Indianapolis, Ind.) for times ranging from 10 seconds to 5 minutes or as necessary.

The purified zvefg4-cee appeared as a single band at about 85 kDa under non-reducing conditions with silver staining, but at about 50 kDa under reducing conditions, suggesting a dimeric form of zvefg4-cee under non-reducing conditions.

Using either 4-1, 4-3 or anti-EE antibody, the purified zvegf4-cee showed the same result as silver staining gel; the 4-3 antibody gave a much weaker signal. However, in addition to recognizing the 85-kDa band under non-reducing conditions and the 50-kDa band under reducing conditions, the 4-2 antibody recognized two bands at 35 kDa and 32 kDa under non-reducing conditions, and two bands at 38 kDa and 35 kDa under reducing conditions. While not wishing to be bound by theory, the smaller bands are likely to be cleaved forms of zvefg4-cee missing the N-terminal portion of the protein that is recognized by the 4-1 antibody.

EXAMPLE 4

The zvegf4 cDNA was cloned into the EcoRV-AscI sites of a modified pAdTrack-CMV (He et al., *Proc. Natl. Acad. Sci. USA* 95:2509–2514, 1998). This construct contains the green fluorescent protein (GFP) marker gene. The CMV promoter driving GFP expression was replaced with the SV40 promoter, and the SV40 polyadenylation signal was replaced with the human growth hormone polyadenylation signal. In addition, the native polylinker was replaced with FseI, EcoRV, and AscI sites. This modified form of pAdTrack-CMV was named pZyTrack. Ligation was performed using a commercially available DNA ligation and screening kit (Fast-Link™ kit; Epicentre Technologies, Madison, Wis.).

Zvegf4 was assayed in an aortic ring outgrowth assay (Nicosia and Ottinetti, *Laboratory Investigation* 63:115, 1990; Villaschi and Nicosia, *Am. J. Pathology* 143:181–190, 1993). Thoracic aortas were isolated from 1–2 month old SD male rats and transferred to petri dishes containing HANK's buffered salt solution. The aortas were flushed with additional HANK's buffered salt solution to remove blood, and adventitial tissue surrounding the aorta was carefully removed. Cleaned aortas were transferred to petri dishes containing EBM basal media, serum free (Clonetics, San Diego, Calif.). Aortic rings were obtained by slicing approximately 1-mm sections using a scalpel blade. The ends of the aortas used to hold the aorta in place were not used. The rings were rinsed in fresh EBM basal media and placed individually in a wells of a 24-well plate coated with basement membrane matrix (MATRIGEL®; Becton Dickinson, Franklin Lakes, N.J.). The rings were overlayed with an additional 50 µl of the matrix solution and placed at 37° C. for 30 minutes to allow the matrix to gel. Test samples were diluted in EBM basal serum-free media supplemented with 100 units/ml penicillin, 100 µg/ml streptomycin and HEPES buffer and added at 1 ml/well. Background control was EBM basal serum-free media alone. Basic FGF (R&D Systems, Minneapolis, Minn.) at 20 ng/ml was used as a positive control. Zvegf4 adenovirus was added to wells, assuming a cell count of 500,000 cells and a multiplicity of infection of 5000 particles/cell. A null adenovirus (designated "zPar") was used as a control. Samples were added in a minimum of quadruplets. Rings were incubated for 5–7 days at 37° C. and analyzed for growth. Aortic outgrowth was scored by multiple, blinded observers using 0 as no growth and 4 as maximum growth. Zvegf4 adenovirus produced a significant increase in outgrowth, comparable to the most potent control (bFGF).

EXAMPLE 5

Recombinant zvegf4 was analyzed for mitogenic activity on rat liver stellate cells (obtained from N. Fausto, University of Washington), human aortic smooth muscle cells (Clonetics Corp., Walkersville, Md.), human retinal pericytes (Clonetics Corp.) and human hepatic fibroblasts (Clonetics Corp.). Test samples consisted of conditioned media (CM) from adenovirally infected HaCaT human keratinocyte cells (Boukamp et al., *J. Cell. Biol.* 106: 761–771, 1988; Skobe and Fusenig, *Proc. Natl. Acad. Sci. USA* 95:1050–1055, 1998; obtained from Dr. Norbert E. Fusenig, Deutsches Krebsforschungszentrum, Heidelberg, Germany) expressing full length zvegf-4. Control CM was generated from HaCaT cells infected with a parental GFP-expressing adenovirus (zPar). The CM were concentrated 10-fold using a 15 ml centrifugal filter device with a 10K membrane filter (ULTRAFREE®; Millipore Corp., Bedford, Mass.), then diluted back to 1× with ITS media (serum-free DMEM/Ham's F-12 medium containing 5 µg/ml insulin, 20 µg/ml transferrin, and 16 pg/ml selenium). Cells were plated at a density of 2,000 cells/well in 96-well culture plates and grown for approximately 72 hours in DMEM containing 10% fetal calf serum at 37° C. Cells were quiesced by incubating them for approximately 20 hours in serum-free DMEM/Ham's F-12 medium containing insulin (5 µg/ml), transferrin (20 µg/ml), and selenium (16 pg/ml) (ITS). At the time of the assay, the medium was removed, and test samples were added to the wells in triplicate. For measurement of [$^3$H]thymidine incorporation, 20 µl of a 50 µCi/ml stock in DMEM was added directly to the cells, for a final activity of 1 µCi/well. After another 24-hour incubation, media were removed and cells were incubated with 0.1 ml of trypsin until cells detached. Cells were harvested onto 96-well filter plates using a sample harvester (FILTER-MATE™ harvester; Packard Instrument Co., Meriden, Conn.). The plates were then dried at 65° C. for 15 minutes, sealed after adding 40 µl/well scintillation cocktail (MICROSCINT™ O; Packard Instrument Co.) and counted on a microplate scintillation counter (TOPCOUNT®; Packard Instrument Co.). Results, presented in Table 2, demonstrated that zvegf4 CM had approximately 7-fold higher mitogenic activity than control CM on pericytes cells and approximately a 1.5–2.4-fold higher mitogenic activity on the other cell types tested.

TABLE 2

|  | CPM incorporated | | | |
| --- | --- | --- | --- | --- |
|  | Zvegf4 (1 × CM) | | zPar (1 × CM) | |
| Sample | Mean | St. dev. | Mean | St. dev. |
| Human retinal pericytes | 3621 | 223 | 523 | 306 |
| Human hepatic fibroblasts | 7757 | 753 | 3232 | 264 |
| Human aortic SMC | 2009 | 37 | 1263 | 51 |
| Rat liver stellate cells | 34707 | 1411 | 14413 | 1939 |

EXAMPLE 6

Recombinant, C terminal glu-glu tagged zvegf4 was analyzed for mitogenic activity on human aortic smooth muscle cells (HAOSMC) (Clonetics), human retinal pericytes (Clonetics) and human aortic adventitial fibroblasts (AoAF) (Clonetics). Cells were plated at a density of 2,000 cells/well in 96-well culture plates and grown for approximately 72 hours in DMEM containing 10% fetal calf serum at 37° C. Cells were quiesced by incubating them for 20 hours in ITS medium. At the time of the assay, the medium was removed, and test samples were added to the wells in triplicate. Test samples consisted of purified, full-length, tagged zvegf4 expressed in baculovirus-infected cells. Purified protein in a buffer containing 0.1% BSA was serially diluted into ITS medium at concentrations of 1 µg/ml to 1 ng/ml and added to the test plate. A control buffer of 0.1% BSA was diluted identically to the highest concentration of zvegf4 protein and added to the plate. For measurement of [$^3$H]thymidine incorporation, 20 µl of a 50 µCi/ml stock in DMEM was added directly to the cells, for a final activity of 1 µCi/well. After another 24-hour incubation, mitogenic activity was assessed by measuring the uptake of [$^3$H]

thymidine. Media were removed, and cells were incubated with 0.1 ml of trypsin until cells detached. Cells were harvested onto 96-well filter plates using a sample harvester (FILTERMATE™ harvester; Packard Instrument Co., Meriden, Conn.). The plates were then dried at 65° C. for 15 minutes, sealed after adding 40 µl/well scintillation cocktail (MICROSCINT™ O; Packard Instrument Co.) and counted on a microplate scintillation counter (TOPCOUNT®; Packard Instrument Co.). Results, presented in Table 3, demonstrated that 80 ng/ml zvegf4 had approximately 1.7-fold higher mitogenic activity on pericytes, 3.2-fold higher activity on aortic SMCs, and 2.6-fold higher activity on aortic fibroblasts as compared to the buffer control.

TABLE 3

| | CPM Incorporated | | | | | |
|---|---|---|---|---|---|---|
| | Pericytes | | HAoSMC | | AoAF | |
| Sample | Mean | St. dev. | Mean | St. dev. | Mean | St. dev. |
| Zvegf4, 80 ng/ml | 96.7 | 18.2 | 488.7 | 29.6 | 177.0 | 1.0 |
| Zvegf4, 20 ng/ml | 81.7 | 11.7 | 211.7 | 50.8 | 107.7 | 20.1 |
| Zvegf4, 5 ng/ml | 67.3 | 6.7 | 191.7 | 4.5 | 123.7 | 10.5 |
| Buffer control | 58.7 | 8.5 | 152.3 | 40.1 | 68.7 | 8.3 |

EXAMPLE 7

Mice (C57BL6) were infected with a zvegf4-encoding adenovirus vector (AdZyvegf4) to determine the effects on serum chemistry, complete blood counts (CBC), body and organ weight changes, and histology. On day -1, the mice were tagged, individually weighed, and group normalized for separation into treatment groups (4 mice per cage). Group 1 mice (n=8 females, 7 males) received GFP (control) adenovirus, $1\times10^{11}$ particles. Group 2 mice (n=8 females, 6 males) received zvegf4 adenovirus, $1\times10^{11}$ particles. Group 3 mice (n=8 females, 8 males) were untreated controls. On day 0, the mice received injections of the appropriate adenovirus solution. On day 10, blood was collected (under ether anesthesia) for CBCs and clinical chemistry measurements. On day 20, mice were weighed and sacrificed by cervical dislocation after collecting blood (under ether anesthesia) for CBCs and clinical chemistry measurements. Tissues were collected for histopathology. Observations were as follows:

Serum chemistry changes: AdZyvegf4 treated mice were hypoglycemic. This effect increased in magnitude over time (day 10 vs. day 20). Serum cholesterol levels were significantly increased (2-fold) at both time points. Serum levels of albumin and the enzymes ALT, AST and alkaline phosphatase were all significantly increased in AdZyvegf4 treated mice. Serum calcium and total bilirubin were also significantly increased, and became more elevated over time.

CBC changes: AdZyvegf4-treated mice had significantly higher lymphocyte count at both time points (mean >10). Platelet counts were significantly lower at day 20. Red blood cell count was significantly higher in females at day 10, significantly higher in males at day 20.

Body/organ weights: AdZyvegf4-treated males lost weight over the course of the experiment. This result was significantly different than control animals, which gained weight. There was no difference among the female mice; all groups gained similar weight. Spleen weight was significantly greater (approximately 4-fold) in all AdZyvegf4-treated mice. Liver weight was also significantly greater in all AdZyvegf4-treated mice. There was no significant difference in kidney weight between groups.

Histology: In the liver, proliferation of sinusoidal endothelial cells was observed. In the spleen, proliferation of reticuloendothelial cells was observed. In the kidney, proliferative glomerulopathy was observed. While not wishing to be bound by theory, this glomerulopathy may have been due to proliferation of capillary endothelial cells. In the femurs, there was proliferation of endosteal bone (mostly in trabecular bone), which in some cases replaced most of the bone marrow. Proliferation of stromal cells was also observed in bone. In the lung, there was increased frequency of brochoaveolar lymphoid tissue.

EXAMPLE 8

90 µg of recombinant zvegf4 protein was dissolved in 500 µl PBS containing 2 mCi Na-$^{125}$I (Amersham Corp.). One derivatized, nonporous polystyrene bead (IODO-BEADS®; Pierce, Rockford, Ill.) was added, and the reaction mixture was incubated one minute on ice. The iodinated protein was separated from unincorporated $^{125}$I by gel filtration using an elution buffer of 10% acetic acid, 150 mM NaCl, and 0.25% gelatin. The active fraction contained 29 µg/ml $^{125}$I-zvegf4 with a specific activity of $3.0\times10^4$ cpm/ng.

The following cell lines were plated into the wells of a 24-well tissue culture dish and cultured in growth medium for three days:
1. Human retinal pericytes, passage 6 (pericytes).
2. Rat stellate cells, passage 8.
3. Human umbilical vein endothelial cells, passage 4 (HUVEC).
4. Human aortic adventicial fibroblasts, passage 5 (AoAF).
5. Human aortic smooth muscle cells, passage 2 (AoSMC).

Cells were washed once with ice-cold binding buffer (HAM'S F-12 containing 2.5 mg/ml BSA, 20 mM HEPES, pH 7.2), then 250 µl of the following solutions was added to each of three wells of the culture dishes containing the test cells. Binding solutions were prepared in 5 mL of binding buffer with 250 pM $^{125}$I-zvegf4 and:
1. No addition.
2. 25 nMzvegf4.
3. 25 nM zvegf3.
4. 25 nM PDGF-AA.
5. 25 nM PDGF-BB The reaction mixtures were incubated on ice for 2 hours, then washed three times with one ml of ice-cold binding buffer. The bound $^{125}$I-zvegf4 was quantitated by gamma counting a Triton-X 100 extract of the cells.

Results, shown in Table 4, indicate binding of zvegf4 to pericytes, stellate cells, AoAF, and AoSMC, but not to HUVEC. The first column represents total CPM $^{125}$I-zvegf4 bound/well. The second column is $^{125}$I-zvegf4 bound/well when blocked with cold ligand. The difference between the two numbers represents specific binding.

TABLE 4

| Cell Type | $^{125}$I-zvegf4 Bound (CPM) | $^{125}$I-zvegf4 Bound w/cold zvegf4 (CPM) |
|---|---|---|
| 1. Pericytes | 3083 +/− 864 | 623 +/− 60 |
| 2. Stellate Cells | 2131 +/− 450 | 413 +/− 164 |
| 3. HUVEC | 485 +/− 91 | 227 +/− 13 |
| 4. AoAF | 1544 +/− 131 | 300 +/− 15 |
| 5. AoSMC | 1628 +/− 203 | 440 +/− 46 |

EXAMPLE 9

The structure of recombinant zvegf4 was analyzed by Western blotting using conventional techniques. Protein produced in the HaCaT human keratinocyte cell line was electrophoresed under reducing and non-reducing conditions, transferred to filters, and probed with antibodies to the interdomain and CUB domain regions of the protein. Reduced protein appeared as a single band having an apparent $M_r$ of approximately 53 kD, consistent with a glycosylated, monomeric protein. Non-reduced protein appeared as a single band having an apparent $M_r$ of approximately 85 kD, consistent with a disulfide-linked dimer.

EXAMPLE 10

Hydroxyethyl cellulose (HEC; dry powder) is reconstituted in 100 mM sodium acetate buffer, pH 6.0 containing 0.2% (w/v) methyl paraben to give a concentration of 1.5% HEC (w/v). The mixture is sterilized by autoclaving at 120° for 20 minutes. Zvegf4 protein is added to a final concentration of 250 µg per gram of gel.

EXAMPLE 11

A 2.5% (w/v) hydroxypropylmethyl cellulose (HPMC) gel is prepared by dissolving powdered HPMC in 100 mM citrate buffer, pH 6.0 containing 0.1% (w/v) methyl paraben. The mixture is sterilized by autoclaving at 120° for 20 minutes. Zvegf4 protein is added to a final concentration of 500 µg per gram of gel.

EXAMPLE 12

Zvegf4 is used to regenerate bone and ligament lost to periodontal disease. Teeth showing 20% to 80% reduction of surrounding jaw bone are scaled, then a full-thickness gingival flap is made by an incision to expose the jaw bone and tooth root. The root is planed to remove bacterial plaque and calculus. Zvegf4 is applied to the periodontal pocket in a 2.5% HPMC gel at a dose of 100 µg per tooth. The gingival flap is then closed and held in place by suturing.

EXAMPLE 13

For regeneration of bone lost to periodontal disease, affected teeth are scaled, and a full-thickness gingival flap is made by incision, exposing the jaw bone and tooth root. The root is planed to remove bacterial plaque and calculus. A solution of zvegf4 in 100 mM sodium acetate buffer, pH 6.0 is added to powdered bone to provide a dosage of 100 µg zvegf4 per tooth. The material is thoroughly mixed and applied to the exposed periodontal pocket. The gingival flap is then closed and held in place by suturing.

EXAMPLE 14

Polylactic acid-polyglycolic acid films (50:50) are solvent cast by dissolving approximately 340 mg of polymer granules (Medisorb Technologies International L.P, Wilmington, De. or Polysciences, Warrington, Pa.) in 10 ml chloroform at room temperature and allowing the solvent to evaporate completely in a slow air flow hood at room temperature. The films are approximately 10 µm thick. Each is cut into a ca. 80 mm×40 mm sheet, resulting in a remaining polymer mass of about 270–290 mg. A solution of zvegf4 and rabbit serum albumin is dispersed on the films, and the liquid is allowed to evaporate. The films are then rolled around 0.9 mm diameter Kirschner wires (K-wires) to provide implants of 1.5 or 3.0 mm diameter as shown in Table 5 and sterilized using cold ethylene oxide gas.

TABLE 5

| Implant Diameter | Zvegf4 (µg) | Albumin (mg) |
|---|---|---|
| 1.5 mm | 100 | 40 |
| 3.0 mm | 10 | 40 |
| 3.0 mm | 100 | 40 |

EXAMPLE 15

To test zvegf4 in an animal model of post-menopausal osteoporosis, seventy three-month-old female Sprague-Dawley rats are weight-matched and divided into seven groups, with ten animals in each group. The study includes a baseline control group of animals sacrificed at the initiation of the study, a control group administered vehicle only, a PBS-treated control group, and a positive control group administered a compound (non-protein or protein) known to promote bone growth. Three dosage levels of zvegf4 protein are administered to the remaining three groups.

Briefly, zvegf4 protein, positive control compound, PBS, or vehicle alone is administered subcutaneously once per day for 35 days. All animals are injected with calcein nine days and two days before sacrifice (two injections of calcein administered each designated day). Weekly body weights are determined. At the end of the 35-day cycle, the animals are weighed and bled by orbital or cardiac puncture. Serum calcium, phosphate, osteocalcin, and CBCs are determined. Both leg bones (femur and tibia) and lumbar vertebrae are removed, cleaned of adhering soft tissue, and stored in 70% ethanol for evaluation. The effect of zvegf4 protein on bone remodeling is performed by peripheral quantitative computed tomography (pQCT; Ferretti, *Bone* 17:353S–364S, 1995), dual energy X-ray absorptiometry (DEXA; Laval-Jeantet et al., *Calcif Tissue Intl.* 56:14–18, 1995; Casez et al., *Bone and Mineral* 26:61–68, 1994) and/or histomorphometry.

EXAMPLE 16

Zvegf4 is tested in acute ovariectomized animals (prevention model) using an in vivo dosing assay with an estrogen-treated group as a control. Eighty three-month-old female Sprague-Dawley rats are weight-matched and divided into eight groups, with ten animals in each group. This includes a baseline control group of animals sacrificed at the initiation of the study; three control groups (sham ovariectomized (sham OVX)+vehicle only; ovariectomized (OVX)+vehicle only; PBS-treated OVX); and a control OVX group that is administered estrogen. Three dosage levels of zvegf4 protein are administered to the remaining three groups of OVX animals.

Since ovariectomy (OVX) induces hyperphagia, all OVX animals are pair-fed with sham OVX animals throughout the 35 day study. Briefly, test compound, positive control compound, PBS, or vehicle alone is administered subcutaneously once per day for 35 days. Alternatively, test compound is formulated in implantable pellets that are implanted for 35 days, or may be administered orally, such as by gastric gavage. All animals, including sham OVX/vehicle and OVX/vehicle groups, are injected intraperitoneally with calcein nine days and two days before sacrifice (two injections of calcein administered each designated day, to ensure proper labeling of newly formed bone). Weekly body weights are determined. At the end of the 35-day cycle, the animals' blood and tissues are processed as described above.

EXAMPLE 17

Zvegf4 is tested in chronic OVX animals (treatment model). 80 to 100 six-month-old female, Sprague-Dawley rats are subjected to sham surgery (sham OVX) or ovariectomy (OVX) at time 0, and 10 rats are sacrificed to serve as baseline controls. Body weights are recorded weekly during the experiment. After approximately 6 weeks of bone depletion (42 days), 10 sham OVX and 10 OVX rats are randomly selected for sacrifice as depletion period controls. Of the remaining animals, 10 sham OVX and 10 OVX rats are used as placebo-treated controls. The remaining OVX animals are treated with 3 to 5 doses of zvegf4 protein for a period of 5 weeks (35 days). As a postitive control, a group of OVX rats is treated with an agent such as PTH, a known anabolic agent in this model (Kimmel et al. *Endocrinology* 132:1577–1584, 1993). To determine effects on bone formation, the femurs, tibiae and lumbar vertebrae 1 to 4 are excised and collected. The proximal left and right tibiae are used for pQCT measurements, cancellous bone mineral density (BMD) (gravimetric determination), and histology, while the midshaft of each tibiae is subjected to cortical BMD or histology. The femurs are prepared for pQCT scanning of the midshaft prior to biomechanical testing. With respect to lumbar vertebrae (LV), LV2 are processed for BMD (pQCT may also be performed); LV3 are prepared for undecalcified bone histology; and LV4 are processed for mechanical testing.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for promoting growth of bone, ligament, or cartilage in a mammal comprising administering to said mammal a composition comprising a pharmacologically effective amount of a protein comprising a first polypeptide disulfide-bonded to a second polpeptide, wherein each of said first and second polypeptides comprises amino acid residues 258–370 of SEQ ID NO:2 and wherein said protein is mitogenic or chemotactic for mesenchymal cells, in combination with a pharmaceutically acceptable delivery vehicle.

2. The method of claim 1 wherein the delivery vehicle is powdered bone, tricalcium phosphate, hydroxyapatite, polymethacrylate, a biodegradable polyester, an aqueous polymeric gel, or a fibrin sealant.

3. The method of claim 1 wherein the composition is locally administered at a site of a bony defect.

4. The method of claim 3 werein the bony defect is a fracture, bone graft size, implant site, or periodontal pocket.

5. The method of claim 1 wherein the composition is administered systemically.

6. The method of claim 1 wherein the protein is covalently linked to a bone targeting agent.

7. The method of claim 1 wherein the composition is locally administered at a joint.

8. The method of claim 1 wherein the composition further comprises a protein selected from the group consisting of insulin-like growth factor 1, platelet-derived growth factor, epidermal growth factor, transforming growth factor-alpha, transforming growth factor-beta, a bone morphogenetic protein, parathyroid hormone, osteoprotegerin, or a fibroblast growth factor.

9. The method of claim 1 wherein each of said first and second polypeptides comprises residues 250–370 of SEQ ID NO:2.

10. The method of claim 1 wherein each of said first and second polypeptides consists of residues 250–370 of SEQ ID NO:2.

* * * * *

UNITED STATES PATENT AND TRADEMARK OFFICE
CERTIFICATE OF CORRECTION

PATENT NO. : 7,192,592 B2
APPLICATION NO. : 10/910938
DATED : March 20, 2007
INVENTOR(S) : Debra G. Gilbertson and Charles E. Hart It is certified that error appears in the above-identified patent and that said Letters Patent is hereby corrected as shown below:

Column 39, line 59, "size" should read --site--.

Signed and Sealed this

Third Day of July, 2007

JON W. DUDAS
*Director of the United States Patent and Trademark Office*

SEQUENCE LISTING

```
<160> NUMBER OF SEQ ID NOS: 9

<210> SEQ ID NO 1
<211> LENGTH: 1882
<212> TYPE: DNA
<213> ORGANISM: Homo sapiens
<220> FEATURE:
<221> NAME/KEY: CDS
<222> LOCATION: (226)...(1338)

<400> SEQUENCE: 1
ccgtcaccat ttatcagctc agcaccacaa ggaagtgcgg cacccacacg cgctcggaaa      60
gttcagcatg caggaagttt ggggagagct cggcgattag cacagcgacc cgggccagcg     120
cagggcgagc gcaggcggcg agagcgcagg gcggcgcggc gtcggtcccg ggagcagaac     180
ccggcttttt cttggagcga cgctgtctct agtcgctgat cccaa atg cac cgg ctc     237
                                                    Met His Arg Leu
                                                      1 atc ttt gtc tac act cta atc tgc gca aac ttt tgc agc tgt cgg gac       285
Ile Phe Val Tyr Thr Leu Ile Cys Ala Asn Phe Cys Ser Cys Arg Asp
  5                  10                  15                  20 act tct gca acc ccg cag agc gca tcc atc aaa gct ttg cgc aac gcc       333
Thr Ser Ala Thr Pro Gln Ser Ala Ser Ile Lys Ala Leu Arg Asn Ala
             25                  30                  35 aac ctc agg cga gat gag agc aat cac ctc aca gac ttg tac cga aga       381
Asn Leu Arg Arg Asp Glu Ser Asn His Leu Thr Asp Leu Tyr Arg Arg
         40                  45                  50 gat gag acc atc cag gtg aaa gga aac ggc tac gtg cag agt cct aga       429
Asp Glu Thr Ile Gln Val Lys Gly Asn Gly Tyr Val Gln Ser Pro Arg
     55                  60                  65 ttc ccg aac agc tac ccc agg aac ctg ctc ctg aca tgg cgg ctt cac       477
Phe Pro Asn Ser Tyr Pro Arg Asn Leu Leu Leu Thr Trp Arg Leu His
 70                  75                  80 tct cag gag aat aca cgg ata cag cta gtg ttt gac aat cag ttt gga       525
Ser Gln Glu Asn Thr Arg Ile Gln Leu Val Phe Asp Asn Gln Phe Gly
 85                  90                  95                 100
```

|  |  |
|---|---:|
| tta gag gaa gca gaa aat gat atc tgt agg tat gat ttt gtg gaa gtt<br>Leu Glu Glu Ala Glu Asn Asp Ile Cys Arg Tyr Asp Phe Val Glu Val<br>　　　　　　　　　　105　　　　　　　　　110　　　　　　　　　115 | 573 |
| gaa gat ata tcc gaa acc agt acc att att aga gga cga tgg tgt gga<br>Glu Asp Ile Ser Glu Thr Ser Thr Ile Ile Arg Gly Arg Trp Cys Gly<br>　　　　120　　　　　　　　　125　　　　　　　　　130 | 621 |
| cac aag gaa gtt cct cca agg ata aaa tca aga acg aac caa att aaa<br>His Lys Glu Val Pro Pro Arg Ile Lys Ser Arg Thr Asn Gln Ile Lys<br>　　　　　　　　　135　　　　　　　　　140　　　　　　　　　145 | 669 |
| atc aca ttc aag tcc gat gac tac ttt gtg gct aaa cct gga ttc aag<br>Ile Thr Phe Lys Ser Asp Asp Tyr Phe Val Ala Lys Pro Gly Phe Lys<br>150　　　　　　　　　155　　　　　　　　　160 | 717 |
| att tat tat tct ttg ctg gaa gat ttc caa ccc gca gca gct tca gag<br>Ile Tyr Tyr Ser Leu Leu Glu Asp Phe Gln Pro Ala Ala Ala Ser Glu<br>165　　　　　　　　　170　　　　　　　　　175　　　　　　　　　180 | 765 |
| acc aac tgg gaa tct gtc aca agc tct att tca ggg gta tcc tat aac<br>Thr Asn Trp Glu Ser Val Thr Ser Ser Ile Ser Gly Val Ser Tyr Asn<br>　　　　　　　　　185　　　　　　　　　190　　　　　　　　　195 | 813 |
| tct cca tca gta acg gat ccc act ctg att gcg gat gct ctg gac aaa<br>Ser Pro Ser Val Thr Asp Pro Thr Leu Ile Ala Asp Ala Leu Asp Lys<br>　　　　200　　　　　　　　　205　　　　　　　　　210 | 861 |
| aaa att gca gaa ttt gat aca gtg gaa gat ctg ctc aag tac ttc aat<br>Lys Ile Ala Glu Phe Asp Thr Val Glu Asp Leu Leu Lys Tyr Phe Asn<br>215　　　　　　　　　220　　　　　　　　　225 | 909 |
| cca gag tca tgg caa gaa gat ctt gag aat atg tat ctg gac acc cct<br>Pro Glu Ser Trp Gln Glu Asp Leu Glu Asn Met Tyr Leu Asp Thr Pro<br>230　　　　　　　　　235　　　　　　　　　240 | 957 |
| cgg tat cga ggc agg tca tac cat gac cgg aag tca aaa gtt gac ctg<br>Arg Tyr Arg Gly Arg Ser Tyr His Asp Arg Lys Ser Lys Val Asp Leu<br>245　　　　　　　　　250　　　　　　　　　255　　　　　　　　　260 | 1005 |
| gat agg ctc aat gat gat gcc aag cgt tac agt tgc act ccc agg aat<br>Asp Arg Leu Asn Asp Asp Ala Lys Arg Tyr Ser Cys Thr Pro Arg Asn<br>　　　　　　　　　265　　　　　　　　　270　　　　　　　　　275 | 1053 |
| tac tcg gtc aat ata aga gaa gag ctg aag ttg gcc aat gtg gtc ttc<br>Tyr Ser Val Asn Ile Arg Glu Glu Leu Lys Leu Ala Asn Val Val Phe<br>　　　　280　　　　　　　　　285　　　　　　　　　290 | 1101 |
| ttt cca cgt tgc ctc ctc gtg cag cgc tgt gga gga aat tgt ggc tgt<br>Phe Pro Arg Cys Leu Leu Val Gln Arg Cys Gly Gly Asn Cys Gly Cys<br>　　　　　　　　　295　　　　　　　　　300　　　　　　　　　305 | 1149 |
| gga act gtc aac tgg agg tcc tgc aca tgc aat tca ggg aaa acc gtg<br>Gly Thr Val Asn Trp Arg Ser Cys Thr Cys Asn Ser Gly Lys Thr Val<br>310　　　　　　　　　315　　　　　　　　　320 | 1197 |
| aaa aag tat cat gag gta tta cag ttt gag cct ggc cac atc aag agg<br>Lys Lys Tyr His Glu Val Leu Gln Phe Glu Pro Gly His Ile Lys Arg<br>325　　　　　　　　　330　　　　　　　　　335　　　　　　　　　340 | 1245 |
| agg ggt aga gct aag acc atg gct cta gtt gac atc cag ttg gat cac<br>Arg Gly Arg Ala Lys Thr Met Ala Leu Val Asp Ile Gln Leu Asp His | 1293 |

-continued

```
              345                 350                 355
cat gaa cga tgc gat tgt atc tgc agc tca aga cca cct cga taa        1338
His Glu Arg Cys Asp Cys Ile Cys Ser Ser Arg Pro Pro Arg
            360                 365                 370 gagaatgtgc acatccttac attaagcctg aaagaacctt tagtttaagg agggtgagat  1398
aagagaccct ttcctacca gcaaccaaac ttactactag cctgcaatgc aatgaacaca   1458
agtggttgct gagtctcagc cttgctttgt taatgccatg gcaagtagaa aggtatatca  1518
tcaacttcta tacctaagaa ataggattg catttaataa tagtgtttga ggttatatat   1578
gcacaaacac acacagaaat atattcatgt ctatgtgtat atagatcaaa tgttttttt   1638 ttttggtata taaccagg tacaccagag gttacatatg tttgagttag actcttaaaa    1698
tcctttgcca aaataaggga tggtcaaata tatgaaacat gtctttagaa aatttaggag  1758
ataaatttat ttttaaattt tgaaacacga aacaatttg aatcttgctc tcttaaagaa   1818
agcatcttgt atattaaaaa tcaaaagatg aggctttctt acatatacat cttagttgat  1878
tatt                                                              1882
```

<210> SEQ ID NO 2
<211> LENGTH: 370
<212> TYPE: PRT
<213> ORGANISM: Homo sapiens

<400> SEQUENCE: 2

```
Met His Arg Leu Ile Phe Val Tyr Thr Leu Ile Cys Ala Asn Phe Cys
 1               5                  10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Glu Ser Asn His Leu Thr Asp
        35                  40                  45

Leu Tyr Arg Arg Asp Glu Thr Ile Gln Val Lys Gly Asn Gly Tyr Val
    50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240
```

```
Leu Asp Thr Pro Arg Tyr Arg Gly Arg Ser Tyr His Asp Arg Lys Ser
            245                 250                 255

Lys Val Asp Leu Asp Arg Leu Asn Asp Asp Ala Lys Arg Tyr Ser Cys
        260                 265                 270

Thr Pro Arg Asn Tyr Ser Val Asn Ile Arg Glu Glu Leu Lys Leu Ala
    275                 280                 285

Asn Val Val Phe Phe Pro Arg Cys Leu Leu Val Gln Arg Cys Gly Gly
290                 295                 300

Asn Cys Gly Cys Gly Thr Val Asn Trp Arg Ser Cys Thr Cys Asn Ser
305                 310                 315                 320

Gly Lys Thr Val Lys Lys Tyr His Glu Val Leu Gln Phe Glu Pro Gly
                325                 330                 335

His Ile Lys Arg Arg Gly Arg Ala Lys Thr Met Ala Leu Val Asp Ile
            340                 345                 350

Gln Leu Asp His His Glu Arg Cys Asp Cys Ile Cys Ser Ser Arg Pro
        355                 360                 365

Pro Arg
    370

<210> SEQ ID NO 3
<211> LENGTH: 1472
<212> TYPE: DNA
<213> ORGANISM: Mus musculus
<220> FEATURE:
<221> NAME/KEY: CDS
<222> LOCATION: (93)...(1205)

<400> SEQUENCE: 3
agggactgtg cagtagaaat ccgccgactc aacccttttgg gctttattta tttacttttg     60
gagcaacgcg atccctaggt cgctgagccc aa atg caa cgg ctc gtt tta gtc     113
                                    Met Gln Arg Leu Val Leu Val
                                      1               5 tcc att ctc ctg tgc gcg aac ttt agc tgc tat ccg gac act ttt gcg     161
Ser Ile Leu Leu Cys Ala Asn Phe Ser Cys Tyr Pro Asp Thr Phe Ala
         10                  15                  20 act ccg cag aga gca tcc atc aaa gct ttg cgc aat gcc aac ctc agg     209
Thr Pro Gln Arg Ala Ser Ile Lys Ala Leu Arg Asn Ala Asn Leu Arg
     25                  30                  35 aga gat gag agc aat cac ctc aca gac ttg tac cag aga gag gag aac     257
Arg Asp Glu Ser Asn His Leu Thr Asp Leu Tyr Gln Arg Glu Glu Asn
 40                  45                  50                  55 att cag gtg aca agc aat ggc cat gtg cag agt cct cgc ttc ccg aac     305
Ile Gln Val Thr Ser Asn Gly His Val Gln Ser Pro Arg Phe Pro Asn
                 60                  65                  70 agc tac cca agg aac ctg ctt ctg aca tgg tgg ctc cgt tcc cag gag     353
Ser Tyr Pro Arg Asn Leu Leu Leu Thr Trp Trp Leu Arg Ser Gln Glu
             75                  80                  85 aaa aca cgg ata caa ctg tcc ttt gac cat caa ttc gga cta gag gaa     401
Lys Thr Arg Ile Gln Leu Ser Phe Asp His Gln Phe Gly Leu Glu Glu
         90                  95                 100 gca gaa aat gac att tgt agg tat gac ttt gtg gaa gtt gaa gaa gtc     449
Ala Glu Asn Asp Ile Cys Arg Tyr Asp Phe Val Glu Val Glu Glu Val
     105                 110                 115 tca gag agc agc act gtt gtc aga gga aga tgg tgt ggc cac aag gag     497
Ser Glu Ser Ser Thr Val Val Arg Gly Arg Trp Cys Gly His Lys Glu
120                 125                 130                 135 atc cct cca agg ata acg tca aga aca aac cag att aaa atc aca ttt     545
Ile Pro Pro Arg Ile Thr Ser Arg Thr Asn Gln Ile Lys Ile Thr Phe
```

-continued

```
            140                 145                 150
aag tct gat gac tac ttt gtg gca aaa cct gga ttc aag att tat tat      593
Lys Ser Asp Asp Tyr Phe Val Ala Lys Pro Gly Phe Lys Ile Tyr Tyr
            155                 160                 165 tca ttt gtg gaa gat ttc caa ccg gaa gca gcc tca gag acc aac tgg      641
Ser Phe Val Glu Asp Phe Gln Pro Glu Ala Ala Ser Glu Thr Asn Trp
            170                 175                 180 gaa tca gtc aca agc tct ttc tct ggg gtg tcc tat cac tct cca tca      689
Glu Ser Val Thr Ser Ser Phe Ser Gly Val Ser Tyr His Ser Pro Ser
        185                 190                 195 ata acg gac ccc act ctc act gct gat gcc ctg gac aaa act gtc gca      737
Ile Thr Asp Pro Thr Leu Thr Ala Asp Ala Leu Asp Lys Thr Val Ala
200                 205                 210                 215 gaa ttc gat acc gtg gaa gat cta ctt aag cac ttc aat cca gtg tct      785
Glu Phe Asp Thr Val Glu Asp Leu Leu Lys His Phe Asn Pro Val Ser
                220                 225                 230 tgg caa gat gat ctg gag aat ttg tat ctg gac acc cct cat tat aga      833
Trp Gln Asp Asp Leu Glu Asn Leu Tyr Leu Asp Thr Pro His Tyr Arg
            235                 240                 245 ggc agg tca tac cat gat cgg aag tcc aaa gtg gac ctg gac agg ctc      881
Gly Arg Ser Tyr His Asp Arg Lys Ser Lys Val Asp Leu Asp Arg Leu
            250                 255                 260 aat gat gat gtc aag cgt tac agt tgc act ccc agg aat cac tct gtg      929
Asn Asp Asp Val Lys Arg Tyr Ser Cys Thr Pro Arg Asn His Ser Val
265                 270                 275 aac ctc agg gag gag ctg aag ctg acc aat gca gtc ttc ttc cca cga      977
Asn Leu Arg Glu Glu Leu Lys Leu Thr Asn Ala Val Phe Phe Pro Arg
280                 285                 290                 295 tgc ctc ctc gtg cag cgc tgt ggt ggc aac tgt ggt tgc gga act gtc      1025
Cys Leu Leu Val Gln Arg Cys Gly Gly Asn Cys Gly Cys Gly Thr Val
                300                 305                 310 aac tgg aag tcc tgc aca tgc agc tca ggg aag aca gtg aag aag tat      1073
Asn Trp Lys Ser Cys Thr Cys Ser Ser Gly Lys Thr Val Lys Lys Tyr
            315                 320                 325 cat gag gta ttg aag ttt gag cct gga cat ttc aag aga agg ggc aaa      1121
His Glu Val Leu Lys Phe Glu Pro Gly His Phe Lys Arg Arg Gly Lys
            330                 335                 340 gct aag aat atg gct ctt gtt gat atc cag ctg gat cat cat gag cga      1169
Ala Lys Asn Met Ala Leu Val Asp Ile Gln Leu Asp His His Glu Arg
345                 350                 355 tgt gac tgt atc tgc agc tca aga cca cct cga taa aacactatgc           1215
Cys Asp Cys Ile Cys Ser Ser Arg Pro Pro Arg
360                 365                 370 acatctgtac tttgattatg aaaggacctt taggttacaa aaaccctaag aagcttctaa   1275
tctcagtgca atgaatgcat atggaaatgt tgctttgtta gtgccatggc aagaagaagc   1335
aaatatcatt aatttctata tacataaaca taggaattca cttatcaata gtatgtgaag   1395
atatgtatat atacttatat acatgactag ctctatgtat gtaaatagat taaatacttt   1455
attcagtata tttactg                                                   1472

<210> SEQ ID NO 4
<211> LENGTH: 370
<212> TYPE: PRT
<213> ORGANISM: Mus musculus

<400> SEQUENCE: 4

Met Gln Arg Leu Val Leu Val Ser Ile Leu Leu Cys Ala Asn Phe Ser
1               5                   10                  15
```

```
Cys Tyr Pro Asp Thr Phe Ala Thr Pro Gln Arg Ala Ser Ile Lys Ala
             20                  25                  30

Leu Arg Asn Ala Asn Leu Arg Arg Asp Glu Ser Asn His Leu Thr Asp
         35                  40                  45

Leu Tyr Gln Arg Glu Glu Asn Ile Gln Val Thr Ser Asn Gly His Val
 50                  55                  60

Gln Ser Pro Arg Phe Pro Asn Ser Tyr Pro Arg Asn Leu Leu Leu Thr
 65                  70                  75                  80

Trp Trp Leu Arg Ser Gln Glu Lys Thr Arg Ile Gln Leu Ser Phe Asp
             85                  90                  95

His Gln Phe Gly Leu Glu Glu Ala Glu Asn Asp Ile Cys Arg Tyr Asp
            100                 105                 110

Phe Val Glu Val Glu Glu Val Ser Glu Ser Ser Thr Val Val Arg Gly
            115                 120                 125

Arg Trp Cys Gly His Lys Glu Ile Pro Pro Arg Ile Thr Ser Arg Thr
            130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Phe Val Glu Asp Phe Gln Pro Glu
                165                 170                 175

Ala Ala Ser Glu Thr Asn Trp Glu Ser Val Thr Ser Ser Phe Ser Gly
            180                 185                 190

Val Ser Tyr His Ser Pro Ser Ile Thr Asp Pro Thr Leu Thr Ala Asp
            195                 200                 205

Ala Leu Asp Lys Thr Val Ala Glu Phe Asp Thr Val Glu Asp Leu Leu
            210                 215                 220

Lys His Phe Asn Pro Val Ser Trp Gln Asp Asp Leu Glu Asn Leu Tyr
225                 230                 235                 240

Leu Asp Thr Pro His Tyr Arg Gly Arg Ser Tyr His Asp Arg Lys Ser
                245                 250                 255

Lys Val Asp Leu Asp Arg Leu Asn Asp Asp Val Lys Arg Tyr Ser Cys
                260                 265                 270

Thr Pro Arg Asn His Ser Val Asn Leu Arg Glu Glu Leu Lys Leu Thr
            275                 280                 285

Asn Ala Val Phe Phe Pro Arg Cys Leu Leu Val Gln Arg Cys Gly Gly
            290                 295                 300

Asn Cys Gly Cys Gly Thr Val Asn Trp Lys Ser Cys Thr Cys Ser Ser
305                 310                 315                 320

Gly Lys Thr Val Lys Lys Tyr His Glu Val Leu Lys Phe Glu Pro Gly
                325                 330                 335

His Phe Lys Arg Arg Gly Lys Ala Lys Asn Met Ala Leu Val Asp Ile
            340                 345                 350

Gln Leu Asp His His Glu Arg Cys Asp Cys Ile Cys Ser Ser Arg Pro
            355                 360                 365

Pro Arg
    370

<210> SEQ ID NO 5
<211> LENGTH: 345
<212> TYPE: PRT
<213> ORGANISM: Homo sapiens

<400> SEQUENCE: 5

Met Ser Leu Phe Gly Leu Leu Leu Leu Thr Ser Ala Leu Ala Gly Gln
 1               5                  10                  15
```

```
Arg Gln Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
            35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
            115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
            195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
            275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345

<210> SEQ ID NO 6
<211> LENGTH: 6
<212> TYPE: PRT
<213> ORGANISM: Artificial Sequence
<220> FEATURE:
<223> OTHER INFORMATION: peptide

<400> SEQUENCE: 6

Glu Tyr Met Pro Thr Asp
1               5

<210> SEQ ID NO 7
```

```
<211> LENGTH: 18
<212> TYPE: PRT
<213> ORGANISM: Artificial Sequence
<220> FEATURE:
<223> OTHER INFORMATION: peptide

<400> SEQUENCE: 7

Cys Gly His Lys Glu Val Pro Pro Arg Ile Lys Ser Arg Thr Asn Gln
 1               5                  10                  15

Ile Lys

<210> SEQ ID NO 8
<211> LENGTH: 25
<212> TYPE: PRT
<213> ORGANISM: Artificial Sequence
<220> FEATURE:
<223> OTHER INFORMATION: peptide

<400> SEQUENCE: 8

Glu Ser Trp Gln Glu Asp Leu Glu Asn Met Tyr Leu Asp Thr Pro Arg
 1               5                  10                  15

Tyr Arg Gly Arg Ser Tyr His Asp Cys
            20                  25

<210> SEQ ID NO 9
<211> LENGTH: 24
<212> TYPE: PRT
<213> ORGANISM: Artificial Sequence
<220> FEATURE:
<223> OTHER INFORMATION: peptide

<400> SEQUENCE: 9

Cys Phe Glu Pro Gly His Ile Lys Arg Arg Gly Arg Ala Lys Thr Met
 1               5                  10                  15

Ala Leu Val Asp Ile Gln Leu Asp
            20
```